United States Patent
De Vlaminck et al.

(10) Patent No.: US 11,781,188 B2
(45) Date of Patent: Oct. 10, 2023

(54) METHODS OF DETECTING CELL-FREE DNA IN BIOLOGICAL SAMPLES

(71) Applicant: CORNELL UNIVERSITY, Ithaca, NY (US)

(72) Inventors: Iwijn De Vlaminck, Ithaca, NY (US); John Richard Lee, Ithaca, NY (US); Philip Smith Burnham, Ithaca, NY (US); Alexandre Pellan Cheng, Ithaca, NY (US); Manikkam Suthanthrian, Ithaca, NY (US); Darshana Dadhania, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 291 days.

(21) Appl. No.: 16/500,929

(22) PCT Filed: Apr. 5, 2018

(86) PCT No.: PCT/US2018/026163
§ 371 (c)(1),
(2) Date: Oct. 4, 2019

(87) PCT Pub. No.: WO2018/187521
PCT Pub. Date: Oct. 11, 2018

(65) Prior Publication Data
US 2020/0048713 A1 Feb. 13, 2020

Related U.S. Application Data

(60) Provisional application No. 62/482,272, filed on Apr. 6, 2017.

(51) Int. Cl.
| | | |
|---|---|---|
| C12Q 1/68 | (2018.01) |
| C12Q 1/6883 | (2018.01) |
| C12Q 1/689 | (2018.01) |
| C12Q 1/70 | (2006.01) |
| C40B 30/06 | (2006.01) |

(52) U.S. Cl.
CPC ......... *C12Q 1/6883* (2013.01); *C12Q 1/689* (2013.01); *C12Q 1/701* (2013.01); *C40B 30/06* (2013.01); *C12Q 2600/154* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS 11,203,784 B2    12/2021   Dor et al.
2015/0133391 A1   5/2015   De Vlaminick et al.

FOREIGN PATENT DOCUMENTS

| WO | WO-2014110493 A1 * | 7/2014 | ........... C12Q 1/6883 |
| WO | WO-2014145340 A2 * | 9/2014 | ........... C12Q 1/6883 |
| WO | WO-2015070086 A1 * | 5/2015 | ............. G16B 30/00 |

OTHER PUBLICATIONS

Hasman et al. J Cin Microbiol. Jan. 2014, vol. 52, No. 1, pp. 139-146. (Year: 2014).*
Burnham et al. (bioRxiv preprint doi: https://doi.org/10.1101/177402; version posted Aug. 17, 2017, pp. 1-24) (Year: 2017).*
Burnham et al. (bioRxiv preprint doi: https://doi.org/10.1101/177402; version posted Jan. 16, 2018, pp. 1-25) (Year: 2018).*
Labugger et al. (Infection 45:269-276; Published online: Oct. 31, 2016) (Year: 2016).*
Gansauge et al. (Nucleic Acids Research, 2017, vol. 45, No. 10, e79, 10 pages) (Year: 2017).*
Gielis et al. (American Journal of Transplantation 2015; 15: 2541-2551) (Year: 2015).*
Brown et al. (Nature Biotechnology, 2016, vol. 34, No. 12, pp. 1256-1263 plus online materials, 12 pages total) (Year: 2016).*
*Mycobacterium tuberculosis* H37Rv, complete genome. Genbank Accession NC_000962. Dec. 14, 2017. 2 pages. (Year: 2017).*
Cheng et al. (Clinical Biochemistry, vol. 50, Issue 9, Jun. 2017, pates 496-501) (Year: 2017).*
Burnham et al. (Sci Rep 6:27859, DOI: 10.1038/srep27859 pp. 1-9) (Year: 2016).*
(Raine et al. Nucleic Acids Research, 2017, vol. 45, No. 6 e36 doi: 10.1093/nar/gkw1110, 15 pages. Published online Nov. 29, 2016) (Year: 2016).*
Schmidt et al. (J Antimicrob Chemother 2017; 72: 104-114) (Year: 2017).*
Moreira et al. (Clinical Biochemistry 42 (2009) 729-731) (Year: 2009).*
Bettegowda, C. et al., "Detection of Circulating Tumor DNA in Early- and Late-Stage Human Malignancies", Feb. 19, 2014, Sci Transl Med, vol. 6, No. 224, 3007094, pp. 1-25.
Cheng, T. H. et al., "Genomewide Bisulfite Sequencing Reveals the Origin and Time-Dependent Fragmentation of Urinary cfDNA", Feb. 2017, Clinical Biochemistry, vol. 50, No. 9, pp. 496-501.
De Vilaminck, I. et al., "Circulating Cell-Free DNA Enables Non-invasive Diagnosis of Heart Transplant Rejection", Jun. 18, 2014, Sci. Transl. Med., vol. 6, No. 241, 241ra77, pp. 1-19.
Fan, H.C. et al., "Noninvasive Prenatal Measurement of the Fetal Genome", Jul. 19, 2012, Nature, vol. 487, No. 7407, pp. 320-324.

(Continued)

*Primary Examiner* — Juliet C Switzer
(74) *Attorney, Agent, or Firm* — Scully, Scott, Murphy & Presser, P.C.

(57) ABSTRACT

The present disclosure is directed to methods of detecting cell-free DNA (cfDNA) in biological samples and using it to quantify organ damage and identify pathogens. In some aspects, the biological samples are from patients who have undergone solid-organ transplantation. The disclosure is also directed to methods of detecting and analyzing methylation patterns in cell-free DNA from organ transplant patients to identify the presence of pathogens as well as quantify contributing tissue proportions as a measurement of the host response.

17 Claims, 21 Drawing Sheets
(20 of 21 Drawing Sheet(s) Filed in Color)
Specification includes a Sequence Listing.

(56) References Cited

OTHER PUBLICATIONS

Gansauge, M. T. & Meyer, M., "Single-Stranded DNA Library Preparation for the Sequencing of Ancient or Damaged DNA", Mar. 14, 2013, Nature Protocols, vol. 8, No. 4, 13 pages.
Hasman, H. et al., "Rapid Whole-Genome Sequencing for Detection and Characterization of Microorganisms Directly from Clinical Samples", Jan. 2014, Journal of Clinical Microbiology, vol. 52, No. 1, 139-146, 9 pages.
Meyer, M. et al., "A High Coverage Genome Sequence from an Archaic Denisovan Individual", Oct. 12, 2012, Science, vol. 338, No. 6104, pp. 222-226.
Quake, S., "Sizing Up Cell-Free DNA", 2012, Clin. Chem., vol. 58, No. 3, pp. 489-490.
Su, Y. H. et al., Human Urine Contains Small, 150 to 250 Nucleotide-Sized, Soluble DNA Derived from the Circulation and May Be Useful in the Detection of Colorectal Cancer, May 2004, The Journal of Molecular Diagnostics, vol. 6, No. 2, pp. 101-107.
Tsui, N. B. et al., "High Resolution Size Analysis of Fetal DNA in the Urine of Pregnant Women by Paired-End Massively Parallel Sequencing", Oct. 2012, PloS one, vol. 7, No. 10, e48319, 7 pages.
International Search Report dated Dec. 12, 2018 together with the Written Opinion received in related International Application No. PCT/US2018/26163.
Beck, J., et al., "Digital Droplet PCR for Rapid Quantification of Donor DNA in the Circulation of Transplant Recipients as a Potential Universal Biomarker of Graft Injury", Clinical Chemistry (2013), Received May 29, 2013; accepted Aug. 19, 2013, pp. 1732-1741, 59:12.
Bolger, A.M., et al., "Trimmomatic: a flexible trimmer for Illumina sequence data", Bioinformatics, 2014, Received on Jul. 13, 2013; revised on Mar. 9, 2014; accepted on Mar. 25, 2014, Advance Access publication Apr. 1, 2014, pp. 2114-2120, vol. 30, No. 15.
Burnham, P., et al., "Single-stranded DNA library preparation uncovers the origin and diversity of ultrashort cell-free DNA in plasma", bioRxiv preprint, Posted Dec. 30, 2015, 28 pages.
Burnham, P., et al., "Single-stranded DNA library preparation uncovers the origin and diversity of ultrashort cell-free DNA in plasma",Scientific Reports, received Feb. 1, 2016, accepted May 26, 2016, Published Jun. 14, 2016, pp. 1-9, 6:27859.
Curradi, M., et al., "Molecular Mechanisms of Gene Silencing Mediated by DNA Methylation", Molecular and Cellular Biology May 2002, Received Dec. 27, 2001, Accepted Jan. 29, 2002, pp. 3157-3173, vol. 22, No. 9.
De Vlaminck, I., et al., "Temporal Response of the Human Virome to Immunosuppression and Antiviral Therapy", Cell, Received May 6, 2013, Revised Aug. 22, 2013, Accepted Oct. 10, 2013, Published Nov. 21, 2013, pp. 1178-1187, 155.
De Vlaminck, I., et al., "Noninvasive monitoring of infection and rejection after lung transplantation", PNAS, Oct. 27, 2015, pp. 13336-13341, vol. 112, No. 43.
Fan, H.C., et al., "Noninvasive diagnosis of fetal aneuploidy by shotgun sequencing DNA from maternal blood", PNAS, Oct. 21, 2008, pp. 16266-16271, vol. 105, No. 42.
Gardiner-Garden, M., et al., "CpG Islands in Vertebrate Genomes", J. Mol. Biol. (1987), Received Nov. 3, 1986 and in revised form Feb. 25, 1987, pp. 261-282, 196.
Grskovic, M., et al., "Validation of a Clinical-Grade Assay to Measure Donor-Derived Cell-Free DNA in Solid Organ Transplant Recipients", The Journal of Molecular Diagnostics, Nov. 2016, Accepted for publication Jul. 8, 2016., pp. 890-902, vol. 18, No. 6.
Karlsson, K., et al., "Amplification-free sequencing of cell-free DNA for prenatal non-invasive diagnosis of chromosomal aberrations", Genomics (2015), Received Dec. 20, 2013, Accepted Dec. 16, 2014, Available online Dec. 24, 2014 pp. 150-158, 105.
Kent, W.J., et al., "BLAT—The BLAST-Like Alignment Tool", Genome Res. 2002, Received Dec. 19, 2001; accepted in revised form Jan. 25, 2002, pp. 656-664, 12.
Kent, W.J., et al., "The Human Genome Browser at UCSC", Genome Res. 2002, Received Dec. 19, 2001; accepted in revised form Apr. 3, 2002, pp. 996-1006, 12.
Korem, T., et al., "Growth dynamics of gut microbiota in health and disease inferred from single metagenomic samples", Science, Sep. 4, 2015, May 1, 2015; accepted Jul. 16, 2015, Published online Jul. 30, 2015, pp. 1101-1106, vol. 349, Issue 6252.
Langmead, B., et al., "Fast gapped-read alignment with Bowtie 2", Nature Methods, Apr. 2012, Received Sep. 23, 2011; accepted Feb. 6, 2012; published online Mar. 4, 2012, pp. 357-360, vol. 9 No. 4.
Lehmann-Werman, R., et al., "Identification of tissue-specific cell death using methylation patterns of circulating DNA", PNAS, Published online Mar. 14, 2016, pp. E1826-E1834.
Li, H., et al., "The Sequence Alignment/Map format and SAMtools", Bioinformatics, 2009, Received on Apr. 28, 2009, revised on May 28, 2009, accepted on May 30, 2009, Advance Access publication Jun. 8, 2009, pp. 2078-2079, vol. 25, No. 16.
Li, H., et al., "Fast and accurate short read alignment with Burrows-Wheeler transform", Bioinformatics, 2009, Received on Feb. 20, 2009, revised on May 6, 2009, accepted on May 12, 2009, Advance Access publication May 18, 2009, pp. 1754-1760, vol. 25, No. 14.
Lo, Y. M. D., et al., "Presence of donor-specific DNA in plasma of kidney and livertransplant recipients", Lancet, May 2, 1998, 3 pages, vol. 351, No. 9112.
Lo, Y.M.D., et al., "Presence of fetal DNA in maternal plasma and serum", Lancet 1997, Aug. 16, 1997, pp. 485-487, vol. 350.
McArthur, A.G., et al., "The Comprehensive Antibiotic Resistance Database", Antimicrobial Agents and Chemotherapy, Jul. 2013, Received Feb. 28, 2013, Returned for modification Mar. 29, 2013, Accepted Apr. 29, 2013, Published ahead of print May 6, 2013, pp. 3348-3357, vol. 57, No. 7.
Nelson, D.E., et al., "Characteristic Male Urine Microbiomes Associate with Asymptomatic Sexually Transmitted Infection", PLoS ONE, Nov. 1, 2010, pp. 1-7, vol. 5, Issue 11, e14116.
Santiago-Rodriguez, T.M., et al., "The human urine virome in association with urinary tract infections", Frontiers in Microbiology, Jan. 2015, Received: Nov. 20, 2014, paper pending published Dec. 3, 2014, accepted Jan. 6, 2015, published online Jan. 23, 2015, pp. 1-12, vol. 6, Article 14, 1.
Snyder, M.W., et al., "Cell-free DNA Comprises an In Vivo Nucleosome Footprint that Informs Its Tissues-Of-Origin", Cell, Jan. 14, 2016, pp. 57-68, 164.
Soetaert, K., et al., "Package limSolve , solving linear inverse models in R", Jan. 2009, pp. 1-22.
Ulz, P., et al., "Inferring expressed genes by whole-genome sequencing of plasma DNA", bioRxiv preprint first posted online Apr. 20, 2016, 25 pages.
Wolfe, A.J., et al., "Evidence of Uncultivated Bacteria in the Adult Female Bladder", Journal of Clinical Microbiology Apr. 2012, Received Nov. 16, 2011 Returned for modification Dec. 27, 2011, Accepted Jan. 12, 2012, Published ahead of print Jan. 25, 2012, pp. 1376-1383, vol. 50, No. 4.
Xia, L.C., et al., "Accurate Genome Relative Abundance Estimation Based on Shotgun Metagenomic Reads", PLoS ONE Dec. 2011, Received Jul. 12, 2011, Accepted Oct. 30, 2011, Published Dec. 6, 2011, pp. 1-13, vol. 6, Issue 12, e27992.
Zhang, J., et al., "Presence of Donor- and Recipient-derived DNA in Cell-free Urine Samples of Renal Transplantation Recipients: Urinary DNA Chimerism", Clinical Chemistry, 1999, Received Jun. 23, 1999, accepted Jul. 21, 1999, pp. 1741-1746, 45:10.

* cited by examiner

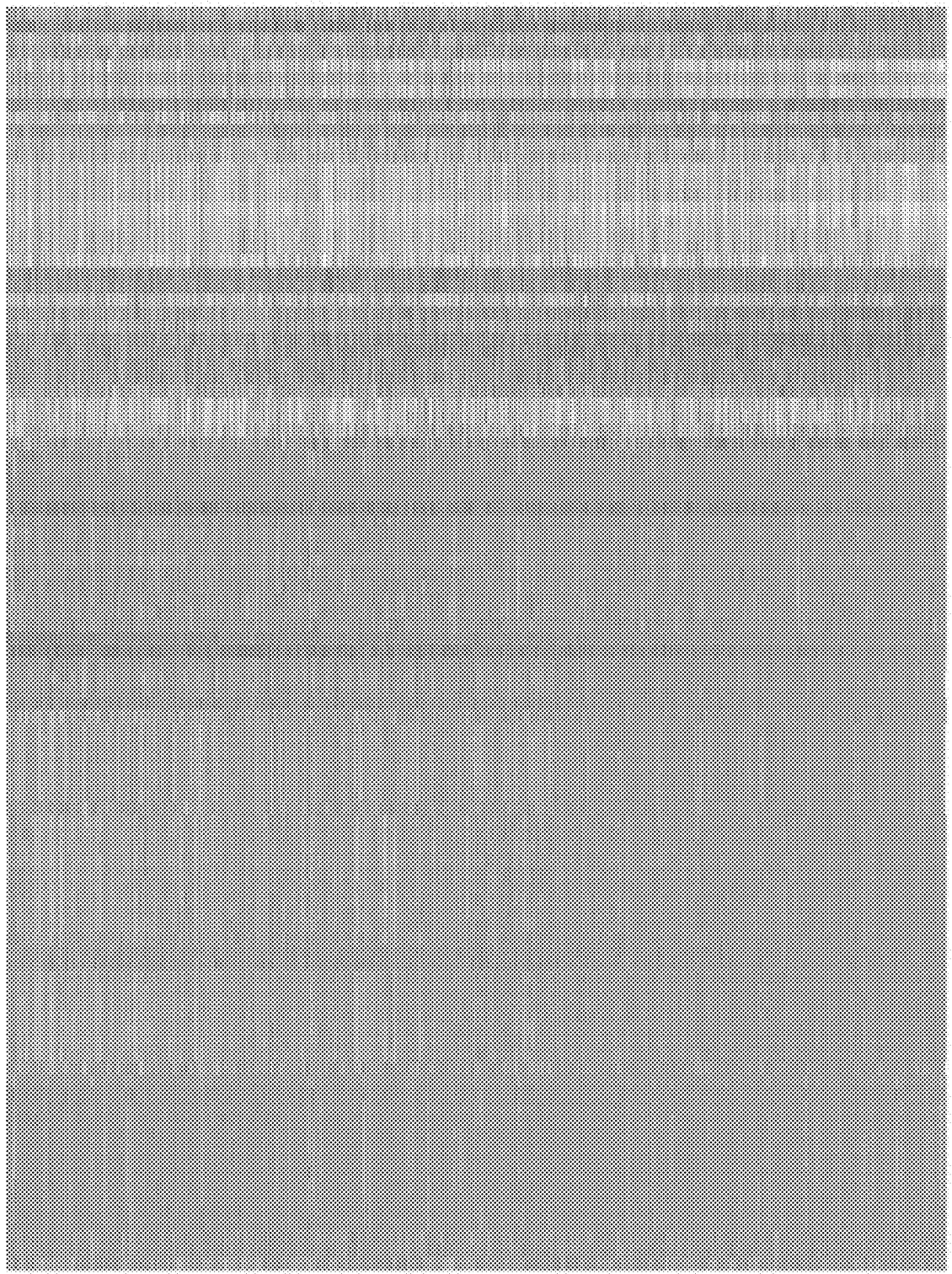
FIG. 7J Cont.'d

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: oligonucleotide
<220> FEATURE:
<221> NAME/KEY: modified_base
<222> LOCATION: (15)..(15)
<223> OTHER INFORMATION: Dideoxycytosine

<400> SEQUENCE: 1
acacgacgct cttcc                                                    15

<210> SEQ ID NO 2
<211> LENGTH: 38
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (35)..(38)
<223> OTHER INFORMATION: N is any one of A, T, G or C

<400> SEQUENCE: 2
gtgactggag ttcagacgtg tgctcttccg atctnnnn                           38

<210> SEQ ID NO 3
<211> LENGTH: 20
<212> TYPE: DNA
<213> ORGANISM: Artificial Sequence
<220> FEATURE:
<223> OTHER INFORMATION: oligonucleotide

<400> SEQUENCE: 3
agatcggaag tttttttttt                                               20

<210> SEQ ID NO 4
<211> LENGTH: 29
<212> TYPE: DNA
<213> ORGANISM: Artificial Sequence
<220> FEATURE:
<223> OTHER INFORMATION: oligonucleotide

<400> SEQUENCE: 4
ggaagagcgt cgtgtaggga aagagtgta                                     29
```

METHODS OF DETECTING CELL-FREE DNA IN BIOLOGICAL SAMPLES

CROSS REFERENCE TO RELATED APPLICATION

This application claims the benefit of priority from U.S. Provisional Application No. 62/482,272, filed Apr. 6, 2017, the entire contents of which are incorporated herein by reference.

STATEMENT REGARDING FEDERALLY SPONSORED RESEARCH OR DEVELOPMENT

This invention was made with government support under Grant Nos. R21A1133331 and R21A1124237, awarded by the National Institutes of Health. The government has certain rights in the invention.

INCORPORATION BY REFERENCE OF SEQUENCE LISTING

The Sequence Listing in an ASCII text file, named as 34855 7811 03 US Sequence Listing.txt of 2 KB, created on Oct. 3, 2019, and submitted to the United States Patent and Trademark Office via EFS-Web, is incorporated herein by reference.

BACKGROUND

Cell-free DNA (cfDNA) exists in many shapes and forms, including fragments of the nuclear genome, the mitochondrial genome and microbial genomes. The predominant type of cfDNA is derived from the nuclear genome and has a fragment size centered around 167 bp, approximately the length of a segment of DNA wound around a histone octamer. These nucleosomal fragments of cfDNA are readily accessible for sequencing using standard library preparation methods that are based on ligation of double strand DNA (dsDNA) sequencing adapters. The most commonly used implementations of this method rely on multiple bead-based size-selective steps that eliminate unwanted adapter-dimer products. These methods, although relevant to a wide range of applications, are not sensitive to the full diversity of circulating DNA; in particular shorter fragments, highly degraded fragments and (partially) single-stranded fragments of DNA in circulation remain undetected.

Transplant recipients are subject to immunosuppressive therapies that reduce the risk of rejection, but increase their susceptibility to opportunistic infections. Analyses of microbial cfDNA in plasma and urine are therefore particularly relevant in the context of transplantation.

Urinary tract infection (UTI) is one of the most common medical problems in the general population (B. Foxman, *Infect. Dis. Clin. North Am.*, vol. 28, no. 1, 1-13, 2014). Among kidney transplant recipients, UTIs occur at an alarmingly high rate (K. C. Abbott et al., *Am. J. Kidney Dis.*, vol. 44, no. 2, 353-362, 2004). The incidence of bacterial UTI is at least 20% in the first three months and 50% in the first 36 months after kidney transplantation. In addition, complications due to viral infection of the urinary tract occur often. An estimated 8% of kidney transplant recipients suffer nephropathy due to BK Polyomavirus infection in the first three years after transplant (H. H. Hirsch et al., *Transplantation*, vol. 79, no. 10, 1277-1286, 2005). The current gold standard for diagnosis of UTI is in vitro culture. Although newer culture methods are being investigated, they, nevertheless, can only detect cultivable organisms, and are insensitive to viral infections. Culture methods are furthermore unable to inform about commensal microbiota and about bacterial growth dynamics. Urinalysis provides a measure for the host's response to UTI and is often required in conjunction with the urine culture to make treatment decisions.

A large number of small fragments of cell-free DNA are present in plasma and urine (S. Quake, *Clin. Chem.*, vol. 58, 489-490, 2012; H. C. Fan et al., *Nature*, vol. 487, no. 7407, 320-4, 2012; Y. M. Dennis Lo et al., *Lancet*, vol. 350, 485-487, 1997). These molecules are the remnants of cell death across the body and offer opportunities for precision diagnostics based on 'omics principles, with applications in a wide range of medical settings, including pregnancy, cancer and solid-organ transplantation (Y. M. Dennis Lo et al., *Lancet*, vol. 350, 485-487, 1997; H. C. Fan et al., *Proc Natl Acad Sci USA*, vol. 105, no. 42, 16266-16271, 2008; I. De Vlaminck et al., *Sci. Transl. Med.*, vol. 6, 241ra77, 2014; C. Bettegowda et al., *Sci Transl Med*, vol. 6, no. 224, 3007094, 2014).

Peritonitis, the inflammation of the peritoneum due to bacterial infection, is a severe complication in peritoneal dialysis (PD) patients and is generally credited as the cause or major contributing factor of death for one in six of these patients (Li et al., *Perit. Dial. Int*, vol. 36 no. 5 481-508. 2016).

DNA cytosine methylation in mammals is a naturally occurring phenomenon where a methyl group is covalently bound to a cytosine. Nearly the complete natural DNA methylation in mammals is restricted to cytosine-guanosine (CpG) dinucleotide palindrome sequences, which are controlled by DNA methyl transferases. CpG dinucleotides are about 1 to 2% of all dinucleotides and are concentrated in so-called CpG islands. A generally accepted definition of CpG islands means that a 200 bp long DNA region has a CpG content of at least 50%, and that the ratio of the number of observed CG dinucleotides and the number of the expected CG dinucleotides is larger than 0.6 (Gardiner-Garden, M., Frommer, M., *J. Mol. Biol.* 196, 261-282 (1987); this cited reference is incorporated by reference in its entirety). Typically, CpG islands have at least 4 CG dinucleotides in a sequence having a length of 100 base pairs.

DNA methylation is involved in gene silencing (M. Curradi, et al., *Mol. Cell. Biol.*, (2002), vol. 22, no. 9, pp. 3157-3173) and its patterns throughout the genome are tissue specific (R. Lehmann-Werman et al., *PNAS*, (2016), vol. 113, no. 13, pp. E1826-1834). Performing bisulfite treatment on DNA will transform unmethylated cytosines into uracils, while methylated cytosines remain unchanged. Through subsequent PCR, the uracils will be amplified as thymines. The entire process of bisulfite treating DNA and creating sequence libraries is referred to as whole-genome bisulfite sequencing (WGBS).

SUMMARY OF THE DISCLOSURE

The present disclosure provides methods comprising the steps of (a) obtaining a sample of a subject at risk of a urinary tract or peritoneal infection, wherein the sample is selected from the group consisting of a urine sample and a peritoneal dialysis fluid sample; (b) preparing a sequencing library from the sample, wherein the sequencing library comprises genomic DNAs present in the sample; (c) sequencing the DNAs in the sequencing library; and (d)

detecting a non-host DNA in the library. In some embodiments, the non-host DNA is a non-human DNA.

In some embodiments, the detecting in step (d) comprises aligning the DNA sequences from step (c) to a human reference genome and removing sequences that align to the human reference genome, wherein the remaining sequences are the non-human DNA sequences.

In some embodiments, the subject is selected from the group consisting of a kidney transplant recipient and a peritoneal dialysis patient.

In some embodiments, the library is a single-stranded sequencing library of cell-free DNA (cfDNA), wherein the cfDNAs in the sequencing library vary between 25 to 350 bp in length.

In some embodiments, the non-human DNA sequences comprise microbial DNA sequences.

In some embodiments, the method further comprises determining the source of the microbial DNA sequences by aligning the sequences to a database of microbial reference genomes. In some embodiments, the method further comprises determining that the subject is undergoing an infection if an increased number of microbial sequences is detected from the sample, compared to a sample of a healthy control.

In some embodiments, the infection is a bacterial infection.

In some embodiments, the method further comprises determining that bacteria causing the bacterial infection are actively replicating if the coverage of the bacterial genome is high and a higher coverage is observed at the bacterial replication origin relative to the rest of the bacterial genome; and determining that bacteria causing the bacterial infection are not replicating if the coverage of the bacterial genome is low and uniform.

In some embodiments, the method further comprises identifying an antibiotic resistance status of the bacteria by aligning the sequences to a database of antibiotic resistance genes. In some embodiments, the method further comprises administering the subject with an antibiotic, wherein the antibiotic is not identified as one of the antibiotics the bacteria are resistant to.

In some embodiments, the infection is a viral infection.

Another aspect of the disclosure provides methods comprising the steps of (a) obtaining a sample of a subject at risk of a urinary tract or peritoneal infection, wherein the sample is selected from the group consisting of a urine sample and a peritoneal dialysis fluid sample; (b) bisulfite treating the sample; (c) preparing a sequencing library from the sample, wherein the sequencing library comprises genomic DNAs present in the sample; (d) sequencing the DNAs in the sequencing library; (e) analyzing the sequences for DNA methylation; and (d) detecting a non-host DNA in the library.

In some embodiments, the step analyzing for DNA methylation comprises determining the tissue of origin of the sequences by aligning the methylation profile of the sequences to a methylation reference panel.

In another aspect, this disclosure is directed to a method of detecting donor DNA in a urine sample from a kidney transplant recipient. In some embodiments, the detection of donor DNA is achieved by the steps comprising (i) aligning the DNA sequences from step (c) to a human reference genome; and (ii) identifying donor DNA from single nucleotide polymorphisms (SNPs) in the sequences that align to the human reference genome that differ from the SNPs in the host genome, wherein is host genome SNP information is derived from a pre-transplant whole blood sample of the subject. In some embodiments, the method further comprises determining the fraction of donor DNA based on the SNP information. In some embodiments, wherein the donor and the recipient are of different sexes and the detection of donor DNA is achieved by the steps comprising (i) aligning the DNA sequences from step (c) to a human reference genome; and (ii) determining fraction of the donor DNA by the ratio of the coverage of the Y chromosome and the coverage of an autosome.

In some embodiments, the donor is a female and the recipient is a male, it is determined that there is donor DNA in the sample if the ratio of chromosome Y coverage to that of the autosome is less than 0.5; it is determined that all the cfDNA in the sample is donor DNA if the ratio of chromosome Y coverage to that of any autosome is zero; and it is determined that there is no donor DNA in the sample if the ratio of chromosome Y coverage to that of any autosome is exactly 0.5.

In some embodiments, the donor is a male and the recipient is a female, and it is determined that there is donor DNA in the sample any DNA sequences align to chromosome Y; it is determined that all the cfDNA in the sample is donor DNA if the ratio of chromosome Y coverage to that of any autosome is exactly 0.5; and it is determined that there is no donor DNA in the sample if the ratio of chromosome Y coverage to that of any autosome is exactly zero.

BRIEF DESCRIPTION OF THE DRAWINGS

The patent or application file contains at least one drawing executed in color. Copies of this paper or patent application publication with color drawing(s) will be provided by the Office upon request and payment of the necessary fee.

DETAILED DESCRIPTION

Definitions

Figures 1A, 1B:
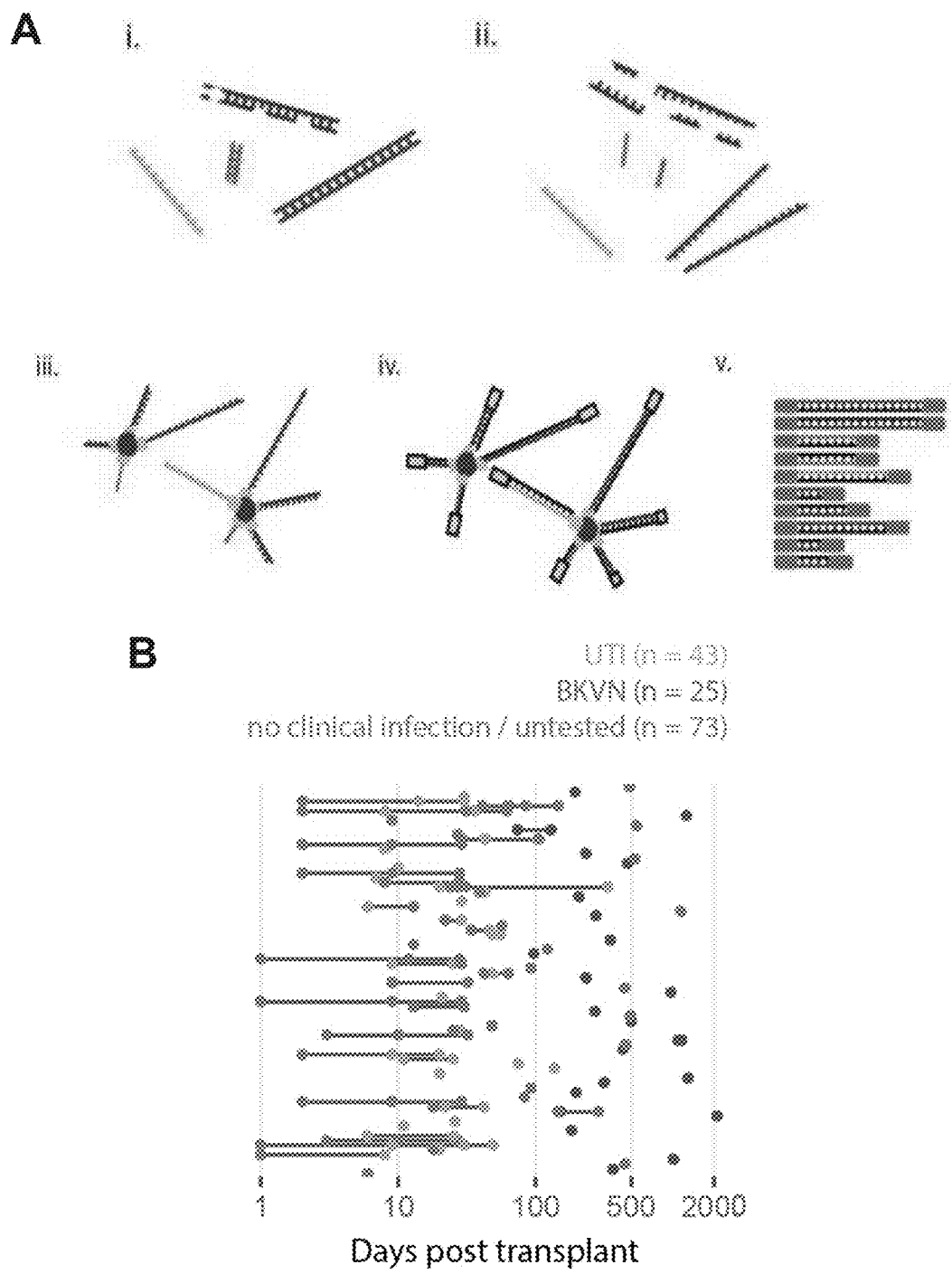
FIGS. 1A-1D. Unbiased sequencing assay and biophysical properties of urinary cfDNA. (A) Schematic representation of the ssDNA library preparation protocol (steps i-v) used for unbiased sequencing of cfDNA in samples. This method using ssDNA libraries allows superior detection of fragmented, small or degraded cfDNA in biological samples. Key steps include: (i) cfDNA isolation, (ii) DNA denaturation, (iii) ssDNA adapter ligation, (iv) extension and double-stranded DNA adapter ligation, (v) and PCR. (B) Overview of post-transplant sample collection dates (color indicates pathology, bars connect samples from same patients). Total samples n=141. Samples from patients diagnosed with urinary tract infection (clinical UTI) n=43. Samples from patients diagnosed with BK virus-associated nephropathy (clinical BKVN) n=25 (C-D) Fragment length density plot measured by paired-end sequencing for different cfDNA types: (C) human chromosomal cfDNA and polyomavirus cfDNA from representative samples, and (D) *E. coli*, parvovirus, and mitochondrial cfDNA from representative samples. Fourier analysis reveals a 10.4 bp periodicity in the fragment length profiles of chromosomal and BK polyomavirus cfDNA (inset C) but not in *E. coli*, parvovirus, and mitochondrial cfDNA (inset D).

As used herein, the term "about" refers to a variation within approximately ±10% from a given value.

The term "acute rejection patients" or the acronym "ARJ" refers to patients who have had an acute rejection of the kidney (either cellular rejection, antibody mediated rejection or both).

The term "autosome" refers a chromosome that is not a sex chromosome.

The term "BK polyomavirus nephropathy-positive patients" or the acronym "BKV" or "BKVN" refers to patients tested positive through kidney biopsy for BK polyomavirus nephropathy. BK virus alone is not necessarily problematic, with people carrying this virus asymptomatically (D. L. Bohl and D. C. Brennan, *Clin. J. Am. Soc. Nephrol.*, vol. 2, no. Supplement 1, pp. S36-S46, July 2007). However, when this virus is symptomatic, it can cause renal dysfunction and other severe complications. This group of patients exhibit BK virus symptoms.

The term "coverage in DNA sequencing" or "depth in DNA sequencing" refers to the number of reads that include a given nucleotide in the reconstructed sequence. "Deep sequencing" refers to the general concept of aiming for high number of replicate reads of each region of a sequence.

The term "early time point patients" or the acronym "ETP" refers to patients who have recently received their transplanted kidney (within the last 14 days), but otherwise exhibit no clinical issues. This cohort is believed to have injury mediated cfDNA release from the graft ("kidney shedding") due to the surgical handling of the kidney.

The term "healthy patients" or the acronym "HLY" refers to patients have received their transplant more than 10 days before sample collection (therefore no longer injury related cfDNA release from the graft) and are otherwise healthy.

The term "relative genomic abundance" refers to the ratio of depth of sequencing of the target genome over the depth of sequencing of the human genome. For instance relative genomic abundance of the BK genome is depth of sequencing of the BK genome over depth of sequencing of the human genome.

The term "ultrashort DNA" refers to DNA molecules shorter than 100 base pairs, e.g., between 25 and 100 base pairs (bp) in length.

The term "urinary tract infection patients" or the acronym "UTI" refers to patients who have a urinary tract infection as diagnosed through standard urine culture.

Subject

In some embodiments, the subject of the present disclosure is someone at risk of an infection. In some embodiments, the subject is at risk of a urinary tract infection. In a specific embodiment, the subject at risk of a urinary tract infection is a kidney transplant patient. In some embodiments, the subject is at risk of a peritoneal infection. In a specific embodiment, the subject at risk of a urinary tract infection is a peritoneal dialysis patient.

Biological Samples

In some embodiments, the biological sample is a urine sample or a peritoneal dialysis fluid sample.

Cell-Free DNA (cfDNA)

Cell-free DNA (cfDNA) refers to DNA molecules found outside a cell. cfDNA is prone to degradation in biological samples due to the unsuitable environment of these samples (e.g., unsuitable pH). In some embodiments, the cfDNA of the disclosure comprises DNA fragments between 25 base pairs (bp) and 350 bp.

In some embodiments, the cfDNA comprises ultrashort DNA fragments between 25-100 bp in length. In some embodiments, the cfDNA comprises fragments of about 25 bp, 30 bp, 40 bp, 50 bp, 75 bp, 100 bp, 150 bp, 200 bp, 250 bp, 300 bp or 350 bp in length.

Construction of ssDNA Sequencing Libraries

In some embodiments, cfDNA is detected in a biological sample. In some embodiments, the detection comprises construction of a single-stranded sequencing library of the genomic DNAs present in the sample. In some embodiments, the detection further comprises sequencing the DNAs in the single-stranded sequencing library.

In some embodiments, a single stranded sequencing library is constructed through the following steps: (1) isolating cfDNA from samples; (2) removing the end phosphates from the cfDNA molecules using an alkaline phosphatase; (3) denaturing the cfDNA into single stranded DNA; (4) adding a biotin-tagged ssDNA adapter to the cfDNA using a DNA ligase; (5) immobilizing the single-stranded cfDNA to a streptavidin coated bead; (6) synthesizing the second strand (complementary strand) of the cfDNA by isothermal amplification, using a primer that hybridizes to the adapter sequence added to the cfDNA in step (4); and (7) adding a double stranded DNA adapter using a DNA ligase. In some embodiments, the present single stranded library preparation method allows superior recovery of ultrashort or damaged cfDNA fragments.

In some embodiments, cfDNA is isolated from samples in step (1) using a nucleic acid purification method. In some embodiments, the nucleic acid purification method is selected from the group consisting of phenol-chloroform extraction, silica-based mini column purification, and Synchronous coefficient of drag alteration (SCODA).

In some embodiments, the alkaline phosphatase used in the removal of phosphate groups from the end of the cfDNA in step (2) is a thermosensitive alkaline phospahatase which is inactivated at a certain temperature. In a specific embodiment, the the alkaline phosphatase used in the removal of phosphate groups from the end of the cfDNA is FastAP thermosensitive alkaline phosphatase (Thermo Fisher).

In some embodiments, the cfDNA is denatured in step (3) to create single-stranded DNA molecules. In some embodiments, denaturation of the DNA is achieved by heating the DNA to above 90° C. In a specific embodiment, the cfDNA is denatured at 95° C.

In some embodiments, the biotin-tagged ssDNA adapter in step (4) is biotin-tagged at the 3' end, and is also phosphorylated at the 5' end. In a specific embodiment, the biotin-tagged ssDNA adapter is CL78 with the following sequence: 5' AGA TCG GAA GTT TTT TTT TT 3' (SEQ ID NO: 3). In some embodiments, the biotin tag is BioTEG (Biotin-TEG, biotin attached to a 15-atom mixed polarity triethylene glycol spacer). In some embodiments, the biotin-tagged ssDNA adapter is ligated to the cfDNA using a DNA ligase. In a specific embodiment, the DNA ligase is Circligase II.

In some embodiments, the biotin adapter-ligated single stranded cfDNA is bound to a streptavidin bead in step (5) through the biotin on the adapter. In some embodiments, the streptavidin bead is magnetic.

In some embodiments, complementary strand of the cfDNA on the beads is synthesized in step (6) using isothermal amplification. In some embodiments, the isothermal amplification comprises the use of a primer that hybridizes to the biotin-tagged DNA adapter. In a specific embodiment, the primer is CL9 with the following sequence: 5' GTG ACT GGA GTT CAG ACG TGT GCT CTT CCG ATC TNN NN 3' (SEQ ID NO: 2), where N is A, T, G or C. In some embodiments, the last 4 N nucleotides in SEQ ID NO: 2 are chemically modified to increase stability.

In some embodiments, a double-stranded DNA adapter is ligated to the double stranded cfDNA on the beads in step (7). In some embodiments, the DNA ligase is a T4 DNA ligase.

In some embodiments, the double stranded adapter in step (7) is prepared by hybridizing two complementrary oligonucleotides. In a specific embodiment, the first complementary oligonucleotide is CL53 with the sequence: 5' ACA CGA CGC TCT TCC 3' (SEQ ID NO: 1), and the second complementary oligonucleotide is CL57 with the sequence 5' GGA AGA GCG TCG TGT AGG GAA AGA GTG TA 3' (SEQ ID NO: 4).

In some embodiments, the last nucleotide of oligonucleotide represented by SEQ ID NO:1 is a Dideoxycytosine (ddC). In some embodiments, SEQ ID NO: 4 is phosphorylated at the 5' end.

In some embodiments, single-stranded sequencing library is prepared according to the protocol described in Gansauge M T. et al. (*Nat. Protoc.*, 8, 737-48 (2013)) with the following differences: (a) Uracils are not removed from DNA sequences (step 1 of Gansauge et al. (*Nat Protoc.*, 2013 April; 8(4):737-48, uracil excision steps), and therefore enzymes Endonuclease VIII or *Archaeoglobus fulgidus* uracil-DNA glycosylase (Afu UDG) are not used; (b) Reduced the amount of reagents, including Circligase buffer II and $MnCl_2$, and enzymes (Circligase II), are used in steps 1 and 5 (the amount of CircLigase II enzyme in the protocol is reduced from 4 µl to 0.8 µl and amounts of $MnCl_2$ and CircLigase II buffer are halved); and (c) some of the adapter primer sequences are modified to more efficiently capture cfDNA (especially ultrashort cfDNA) and reduce cost. In some embodiments, extension primer CL9 is edited to have an addition N*N*N*N overhang (4 random nucleotides comprising any combination of A, T, G or C) on the 3' end to prevent formation of adapter-dimers. In a specific embodiment, the modified CL9 adapter has the following sequence: 5' GTG ACT GGA GTT CAG ACG TGT GCT CTT CCG ATC T*N*N*N*N 3' (SEQ ID NO: 2). In some embodiments, CL53 is modified to have a Dideoxycytosine (ddC) base at the 3' end. In a specific embodiment, modified CL53 has the following sequence: 5' ACA CGA CGC TCT TC/3ddC/3' (SEQ ID NO: 1) (/3ddC/means Dideoxy-C at the 3' end). In some embodiments, CL78 is modified to have oligo T at the 3' end (instead of 10 C3 spacers of the CL78 used by Gansauge M T. et al. (*Nat. Protoc.*, 8, 737-48 (2013))): 5' AGA TCG GAA GTT TTT TTT TT 3' (SEQ ID NO: 3).

In some embodiments, sequencing is achieved by next-generation sequencing. In some embodiments, the next-generation sequencing is chosen from the group consisting of pyrosequencing, single-molecule real-time sequencing, sequencing by synthesis, sequencing by ligation (SOLID sequencing) or nanopore sequencing.

In some embodiments, the detection of cfDNA in the sample further comprises aligning the DNA sequences from the next-generation sequencing to a human reference genome. In a specific embodiment, the human reference genome is GRCh37 (UCSC version hg19) or GRCh38 (UCSC version hg38).

Detection of Infection in Samples Using Next-Generation Sequencing of cfDNA

In some embodiments, the disclosure is directed to methods of detecting infections in the sample. In some embodiments, the methods comprise next-generation sequencing of a single stranded sequencing library made from the cfDNA in the sample. In some embodiments, the method of detecting infections comprises removing the DNA sequences that align to a reference human genome and identifying the remaining non-aligning sequences as non-human DNA sequences.

In some embodiments, the non-human DNA sequences comprise microbial sequences. In some embodiments, the microbial sequences are bacterial sequences or viral sequences.

Identifying the Source of the Microbial Sequences in Biological Samples

In some embodiments, the disclosure is directed to methods of identifying the source of the microbial sequences in the next-generation sequencing results of the cfDNA by aligning the non-human sequences in the sample (i.e., the sequences that do not align to the reference human genome) to a database of microbial reference genomes.

In some embodiments, the method of detecting infections comprises determining that the subject is undergoing an infection if an increased number of non-human sequences align to at least one microbial genome in the database of microbial reference genomes, compared to a sample of a healthy control. In some embodiments, the healthy control is a subject who does not show any symptoms of any infectious disease. In some embodiments, the non-human DNA sequences comprise microbial sequences. In some embodiments, the microbial sequences are bacterial sequences or viral sequences.

Determining the Replication Status of Infecting Bacteria

Bacteria have circular genomes, and bacterial genome replication begins from bacterial replication origins. When a bacterial population is actively replicating, more bacteria in the population are replicating their genomes. Due to the fact that each bacteria begins replicating their DNA from the origin of replication and also that there are bacteria at different stages of replication at any given time, there are more copies of the origin of replication of the bacterial genome compared to the terminal region of the bacterial genome when bacteria are actively replicating. The term "terminal region of the bacterial genome" refers to the region of the bacterial genome which is replicated the latest. In contrast, when bacteria are dormant (i.e., not actively dividing/replicating), less copies of the bacterial genomes are made and the replication is more uniform between the bacterial replication origins and the terminal regions.

In some embodiments, the microbial infection is a bacterial infection, and the disclosure is directed to methods of determining the replication status of infecting bacteria. The method comprises determining that bacteria causing the infection are actively replicating if there is high coverage of the bacteria's genome in the next-generation sequencing of the non-human DNA (i.e., there are many copies of the bacterial genome, so more copies of the bacterial genome are detected by next-generation sequencing after subtracting or removing the human sequences from the next-generation sequencing data) and a higher coverage is observed at the bacterial replication origin relative to the rest of the bacterial genome (i.e., more numbers of sequences align to the bacterial replication origin than to the rest of the bacterial genome, see FIG. 3A and FIG. 3E, top panels). In a specific embodiment, it is determined that the infecting bacteria actively replicating when a higher coverage is observed at the bacterial replication origin relative to the terminal region of the bacterial genome. The method further comprises determining that bacteria causing the bacterial infection are not replicating if the coverage of the bacterial genome is low (i.e., there are fewer number of copies of the bacterial genome, so more fewer copies of the bacterial genome are detected by next-generation sequencing) and uniform (i.e., about the same number of sequences align to the bacterial replication origin as compared to the rest of the bacterial genome, see FIG. 3E, bottom panels. The term "about the same numbers of sequences" means that numbers of aligning sequences are within 10% of each other).

Determining the Antibiotic Resistance Status of Infecting Bacteria

In some embodiments, the microbial infection is a bacterial infection, and the disclosure is directed to methods of determining the antibiotic resistance status of infecting bacteria. In some embodiments, the disclosure is directed to the determining of antibiotic resistance comprises aligning the non-human sequences in the next-generation sequencing results of the cfDNA in the sample (i.e., the sequences that do not align to the reference human genome) to a database of antibiotic resistance genes, and determining the antibiotic resistance based on which antibiotic resistance genes the non-human sequences align to.

In some embodiments, if a non-human sequence aligns to a particular antibiotic resistance gene in the database of antibiotic resistance genes, it is determined that the bacteria in the sample are resistant to said particular antibiotic. In some embodiments, if no sequence aligns to a particular antibiotic resistance gene in the database of antibiotic resistance genes, it is determined that the bacteria in the sample is not resistant (i.e. sensitive) to said particular antibiotic. In some embodiments, as a result of such determination of antibiotic resistance profile in the sample, the patient from whom the sample is taken is treated with an antibiotic that the microbes are not resistant to/are sensitive to.

Detection of Donor DNA in Samples from Organ Transplant Recipients

In some embodiments, the biological sample is from a subject who is an organ transplant recipient. After an organ transplant, some cells in the transplanted organ may release cfDNA into biological fluids. Donor specific cfDNA is present in the circulation of organ transplant recipients and the proportion of donor specific cfDNA is predictive of acute rejection.

An aspect of this disclosure is directed to methods of detecting donor DNA (aka. donor specific cfDNA) in biological samples from organ transplant recipients using next-generation sequencing of cfDNA in those samples. In some embodiments, the method is directed to determining the donor DNA fraction in a sample. In general, a higher donor DNA fraction in a sample represents higher cell death or rejection of the transplanted organ. It is normal to detect a high fraction of donor DNA in biological samples in the first weeks (up to 3-5 weeks) following organ transplantation.

In some embodiments, the subject is a kidney transplant recipient. In some embodiments, the sample is a urine sample.

Determination of Donor DNA Fraction when Organ Donor and Organ Recipient are Sex-Mismatched In some embodiments, the organ donor and the organ recipient are sex-mismatched, i.e. the donor and the recipient are of different sexes. In such cases, the donor DNA fraction in the whole cfDNA in a sample is determined by comparing the coverage of chromosome Y in the next-generation sequencing data to the coverage of an autosome (any one of chromosomes 1-22) in the next-generation sequencing data. In a sample from a male subject, the ratio of the coverage of the Y chromosome over an autosome is 0.5, because there is one copy of the Y chromosome and two copies of any autosome. In a female subject, the ratio of the coverage of the Y chromosome over an autosome is exactly zero, because there is no Y chromosome in a female.

In some embodiments, the organ donor is a female and the organ recipient is a male, and it is determined that there is donor DNA in the sample if the ratio of chromosome Y coverage to that of any autosome is less than 0.5. In some embodiments, the organ donor is a female and the organ recipient is a male, and it is determined that all the cfDNA in the sample is donor DNA if the ratio of chromosome Y coverage to that of any autosome is zero (i.e., no coverage of chromosome Y is detected). In some embodiments, the organ donor is a female and the organ recipient is a male, and it is determined that there is no donor DNA in the sample if the ratio of chromosome Y coverage to that of any autosome is exactly 0.5.

In some embodiments, the organ donor is a male and the organ recipient is a female, and it is determined that there is donor DNA in the sample if there is any coverage of chromosome Y in the sequencing data. In some embodiments, the organ donor is a male and the organ recipient is a female, and it is determined that all the cfDNA in the sample is donor DNA if the ratio of chromosome Y coverage to that of any autosome is exactly 0.5. In some embodiments, the organ donor is a male and the organ recipient is a female, and it is determined that there is no donor DNA in the sample if the ratio of chromosome Y coverage to that of any autosome is exactly zero (i.e., no coverage of chromosome Y is detected).

Detection of Donor DNA Using Single Nucleotide Polymorphism (SNP) Analysis

In some embodiments, donor DNA fraction is determined by a SNP analysis of the next-generation sequencing data from a biological sample and comparing it to the host genome SNP information. In some embodiments, host genome SNP information is derived from a pre-transplant tissue sample from the subject. In a specific embodiment, the tissue sample is a whole blood sample.

In some embodiments, the host genome SNP information is derived by (i) sequencing the host genomic DNA, (ii) aligning the host genomic DNA to a human reference genome, and (iii) determining single nucleotide polymorphisms (SNPs) of the host genome.

In some embodiments, the method of SNP analysis of the next-generation sequencing data comprises (i) constructing a single-stranded sequencing library of the cfDNA present in the sample, (ii) sequencing the DNAs in the single-stranded sequencing library, (iii) aligning the DNA sequences from the next-generation sequencing to a human reference genome, (iv) determining single nucleotide polymorphisms (SNPs) of the cfDNA in the sample. In some embodiments, the method of SNP analysis further comprises (v) comparing the SNP information of the cfDNA in the sample to the SNP information of the host genome. In a specific embodiment, the human reference genome is selected from the group consisting of GRCh37 (UCSC version hg19) and GRCh38 (UCSC version hg38). In some embodiments, sequencing is achieved by next-generation sequencing. In some embodiments, the next-generation sequencing is chosen from the group consisting of pyrosequencing, single-molecule real-time sequencing, sequencing by synthesis, sequencing by ligation (SOLID sequencing) or nanopore sequencing.

Methylation Analysis by Whole-Genome-Bisulfite Sequencing

In some embodiments, methylation patterns are determined by Whole-Genome-Bisulfite Sequencing (WGBS). As used herein, the term "methylation pattern" refers to the presence or absence of methylation of one or more nucleotides.

Figure 7A:
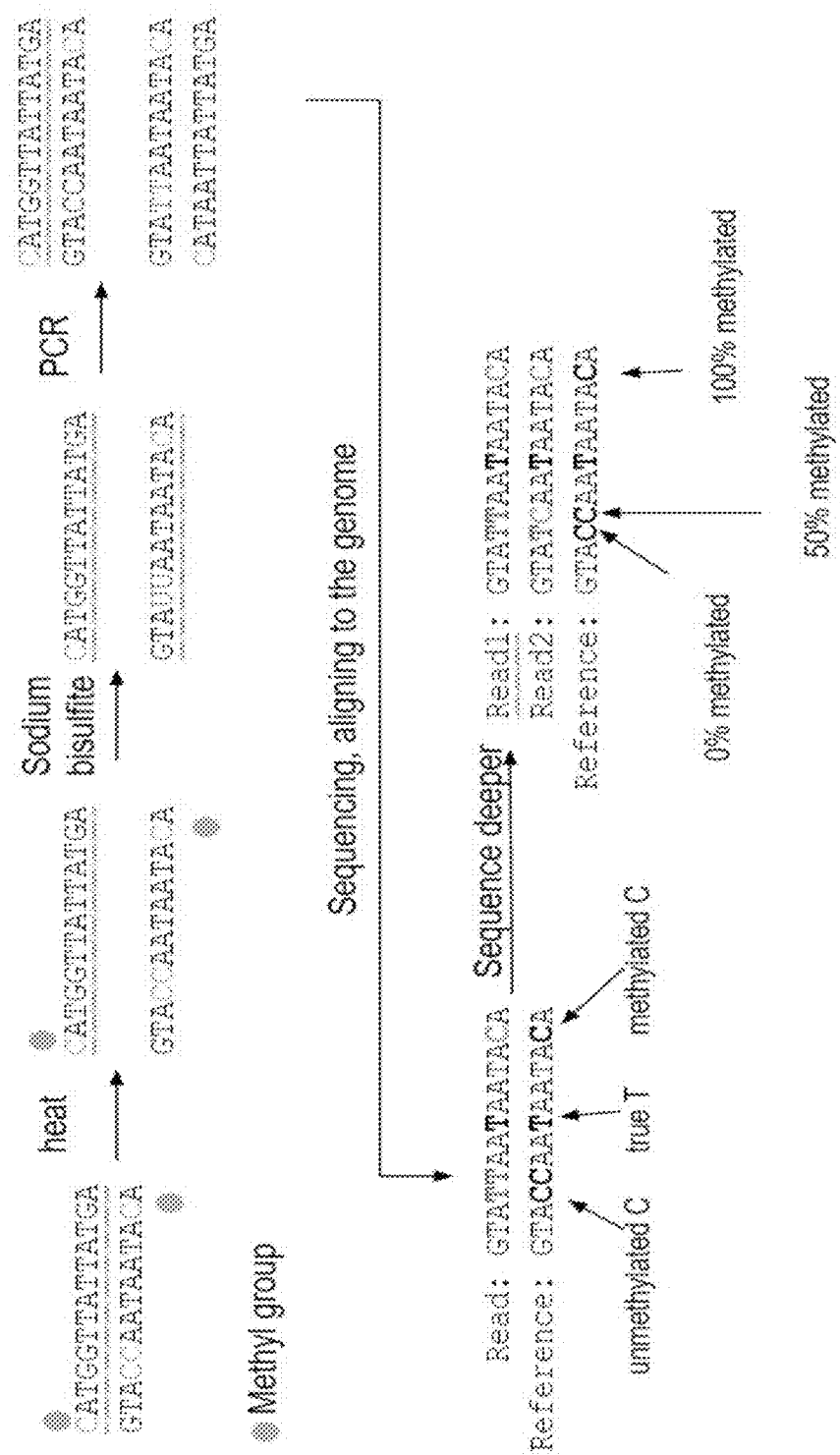
FIGS. 7A-7J. (A) Brief overview of whole-genome bisulfite sequencing. (B) Unsupervised clustering of publicly available whole genome bisulfite-treated tissue samples (WGBS) show that each tissue has a specific methylation signature. WBC=white blood cells. (C) Hypothetical example of how the composition of an unknown bisulfite-treated cfDNA sample can be determined by comparing to reference WGBS profiles. In this example, it is assumed that the sample (pink) contains only DNA from references A (red), B (blue) and C (green). The three references each have their unique methylation pattern throughout the genome. If the collected sample shows 0.6× the methylation pattern of reference A, 0.1× the methylation pattern of reference B and 0.3× the methylation pattern of reference A, then it is known that the sample contained cell-free DNA coming from reference A (60%), B (10%) and C (30%). (D) Scatterplot of the measured kidney percentage versus donor fraction. The NA group shows patients who were not sex-mismatched (included in the figure for completeness). Pearson's product-moment correlation is approximately 0.899 with p-value 7.453e-15. Kidney DNA is determined by methylation analysis as in (C) Donor fraction is determined using the percentage of Y chromosome compared to the autosomal chromosomes. (E) Donor DNA fraction in the urine of patients. BKV: BK virus-infected, ETP: Early time point patients, HLY: Healthy individual, UTI: Urinary Tract Infection, ARJ: Acute rejectors of transplanted kidney. Damage to the transplanted kidney increases the fraction of donor DNA found in the urine, except in UTI cases, where the presence of immune cells during infection skews the ratio towards host. The ETP and HLY cohorts are divided simply based on the time between sample collection and transplant date. (F) Kidney DNA fraction in the urine of patients. BKV: BK virus-infected, ETP: Early time point, HLY: Healthy individual, UTI: Urinary Tract Infection, ARJ: Acute rejectors of transplanted kidney. Patients with BKV nephropathy (BKV) displayed the highest amount of kidney-derived cfDNA, followed by the early time point (ETP) group. Patients with UTIs have the overall lowest amount of kidney derived DNA percentage, potentially due to the overwhelming proportion of infiltrating immune cells. (G) Violin plots of BK Polyomavirus cfDNA sequence abundance (relative genome equivalents, RGE) for patients that are BKVN positive per needle biopsy of the kidney allograft, and patients that are BKVN negative per biopsy using bisulfite-treated samples. Bisulfite-treatment does not prevent detection of BK Polyomavirus cfDNA sequence abundance. (H) Plot of kidney DNA fraction versus BK genomic abundance. The more BK virus is present in a patient, the more fraction of the DNA detected as cfDNA is from the kidney, released as a result of kidney damage. In green, stable patients have low BK relative genome abundance and low kidney DNA in the samples. In red, BKV nephropathy (infectious disease) patients demonstrate high amounts of kidney DNA and high BK relative genome abundance in the samples. (I) Simulated expected results of kidney cfDNA contribution versus BK virus relative genomic abundance in healthy subjects (BK-/BKVN-, orange), BK-infected and symptomatic patients (BK+/BKVN+, blue), and asymptomatic BK patients (BK+/BKVN-, green). (J) Methylation patterns of each reference tissue used in the tissue methylation panel. Genomic locations are sorted by mean methylation and tissues are sorted by hierarchical clustering using Euclidean distance.

An aspect of the present disclosure is directed to determining the tissue of origin of a sample by comparing the methylation profile of the sample to a collection of genome-wide methylation patterns of reference tissues. In some embodiments, the collection of genome-wide methylation patterns of reference tissues is the tissues listed in FIG. 7J.

In some embodiments, the detection of DNA methylation patterns is used to diagnosing a disease, prognosing a disease, predicting a treatment response, diagnosing a predisposition for a disease, diagnosing a progression of a disease, grading a disease, staging a disease, classifying a disease, characterizing a disease, or for identifying a new marker associated with a disease. In some embodiments, the methylation pattern of the genomic DNA in a sample is determined by treating the sample with reagent that differentiates between methylated and unmethylated cytosines. In some embodiments, this reagent is a bisulfite reagent which leads to a conversion of unmethylated cytosines to uracil while methylated cytosines remain unchanged.

In some embodiments, methylation patterns are used to perform unsupervised clustering analysis to reveal similarities and differences between samples. In some embodiments, methylation patterns are used to probe global and local methylation patterns throughout the genome, most notably near transcriptional start sites (TSS) (CpG islands are generally found near TSS).

In some embodiments, WGBS is used to calculate donor cfDNA fraction in a sample from a subject and the subject is an organ transplant patient. In a specific embodiment the subject is a kidney transplant patient. In a specific embodiment the sample is a urine sample.

Determination of the Tissue of Origin DNA in Biological Samples Using WGBS

In some embodiments, WGBS analysis is used to determine tissue of origin from a given bodily-fluid samples (ex: urine, plasma). Donor fraction can be only be used to measure the percent (%) contribution of the transplanted organ to the total cfDNA in the sample, whereas tissue of origin is a systemic measurement (transplanted organ+original host organs/tissues).

In some embodiments, methylation analysis allows measuring the percent contribution of each tissue in a given sample. For example, in kidney transplant recipients, an increase in kidney-derived cfDNA in urine samples might be caused by BKV nephropathy. Because Whole-Genome-Bisulfite Sequencing can also detect presence of a pathogen, this method can be used to detect presence of virus/bacteria (infection), and also see if it is causing a host response (infectious disease).

In some embodiments, a reference-based method is used to calculate the cfDNA's tissue of origin. As methylation patterns are tissue-specific, it is possible to compare the sample's methylation scores to a reference panel in order to infer the relative contribution of each tissue. FIG. 7C indicates the simplified idea behind this calculation.

In some embodiments, tissue of origin of a cfDNA in a biological sample is determined using the following equation:

$$\begin{bmatrix} M_{11} & M_{21} & \ldots & M_{N1} & 1 \\ M_{12} & M_{22} & \ldots & M_{N2} & 1 \\ \vdots & \vdots & \vdots & \vdots & \vdots \\ M_{1(L-1)} & M_{2(L-1)} & \ldots & M_{N(L-1)} & 1 \\ M_{1L} & M_{2L} & \ldots & M_{NL} & 1 \end{bmatrix} \begin{bmatrix} p_1 \\ p_2 \\ \vdots \\ p_N \\ \varepsilon \end{bmatrix} = \begin{bmatrix} O_1 \\ O_2 \\ \vdots \\ O_N \\ O_{N+1} \end{bmatrix}$$

Where M is the methylation score for N tissues over L 500 bp windows. E refers to possible noise, p refers to each tissue's contribution to the cfDNA found in urine (which must always be greater or equal to zero). 0 refers to the observed methylation after sequencing. A parameter is also set that the sum of all tissue contributions cannot exceed 100%.

As there are more genomic windows (~100,000,000) than there are reference tissues for any given sample, windows can be selected to minimize the error defined by the absolute difference between the calculated methylation proportions and the observed methylation. In some embodiments, these equations are solved using quadratic programming. In a specific embodiment, the equations are solved using R programming and the LimSolve package (Soetaert, Karline, Karel Van den Meersche, and Dick Van Oevelen. *"Package limSolve, solving linear inverse models in R."* See http://cran.r-project.org/web/packages/limSolve (2009)).

In some embodiments, the tissue methylation reference panel is created by using tissues that were whole-genome bisulfite sequenced by various laboratories and where the methylation scores were made publicly available. In some embodiments, tissues selected for the reference panel include white blood cell types (eosonophils, neutrophils, etc.), brain, kidney, liver, skin, ovary, testes, colon, and pancreas.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1: Materials and Methods

Study Design and Sample Collection.

113 (1 mL) urine samples and 10 (4 mL) urine samples from a cohort of kidney transplant patient. Urine was stored at −80° C. and was only thawed when ready for extraction. Cell-free DNA was extracted from one (BK virus-associated nephropathy (BKVN), Urinary Tract Infection (UTI) and UTI control) or four mL (BKVN control only) of urine using Qiagen Circulating Nucleic Acid Kit according to the manufacturer's instructions. Following extraction, libraries were prepared from extracted DNA using a single-stranded adapter ligation (P. Burnham et al., Sci. Rep., vol. 6, 27859, 2016).

cfDNA Extraction from Urine.

Urine supernatants are thawed and centrifuged. cfDNA was extracted using the QIAamp circulating nucleic acid kit (Qiagen Valencia, Calif.). The concentration of total cfDNA in the sample was measured using a QuBit fluorometer. cfDNA extracts were stored at −20° C.

Negative Control.

To control for environmental and sample-to-sample contamination, a known-template control sample (IDT-DNA synthetic oligo mix, lengths 25, 40, 55, 70 bp, 0.20 µM eluted in TE buffer) was included in every sample batch and sequenced to approximately 25% of the depth of the cfDNA extracts (~5 million fragments). The five most abundant genera detected across the 23 microbiome controls consisted of *Propionibacterium* (22.9%), *Salmonella* (10.9%), *Pseudomonas* (7.7%), polyomavirus (5.4%), and *E. coli* (5.2%). The mean representation of each genus in the control was used to filter out genera in samples identified as possible contaminants. Possible sources of contamination in these experiments include: environmental contamination during sample collection in the clinic, nucleic acid contamination in reagents used for DNA isolation and library preparation, sample-to-sample contamination due to Illumina index switching.

ssDNA Library Preparation and Next Generation Sequencing.

Sequencing libraries were prepared using a single-stranded library preparation method optimized for the analysis of ultrashort and fragmented DNA, as described in detail in Gansauge et al. (*Nat Protoc.*, 2013 April; 8(4):737-48), with the following differences: (a) The inventors did not remove uracils from the DNA sequences (step 1 of Gansauge et al. (*Nat Protoc.*, 2013 April; 8(4):737-48, uracil excision steps), and therefore did not include the enzymes Endonuclease VIII or *Archaeoglobus fulgidus* uracil-DNA glycosylase (Afu UDG); (b) the inventors reduced the amount of reagents including Circligase buffer II and $MnCl_2$, and enzymes (Circligase II) used in steps 1 and 5 (the amount of CircLigase II enzyme in the protocol was reduced from 4 µl to 0.8 µl and amounts of $MnCl_2$ and CircLigase II buffer were halved); and (c) the inventors changed some of the adapter sequences to more efficiently capture cfDNA and reduce cost. Specifically, extension primer CL9 was edited to have an addition N*N*N*N overhang on the 5' end to prevent formation of adapter-dimers. See SEQ ID NO: 2 below.

Modified CL9:
(SEQ ID NO: 2)
5' GTG ACT GGA GTT CAG ACG TGT GCT CTT CCG ATC T*N*N* N*N 3'

CL53 was edited to have Dideoxycytosine (ddC) at the 3' end. ddC is a dideoxyribonucleoside, and is a synthetic analog of deoxycytosine. The difference between the two is that, in ddC, both the 2'- and 3'-positions of the ribose have a hydrogen (—H) group substituted for the —OH group, whereas in dC, only the 2'-position is so substituted. Blocking the 3'-end in this manner prevents the oligo from either circularization (by self-ligation) or concatemerization to other 5'-App oligos. See SEQ ID NO: 1 below.

Modified CL53:
(SEQ ID NO: 1)
5' ACA CGA CGC TCT TC/3ddC/3'

CL78 was modified to have oligo T (ten Ts) at the 3' end instead of ten C3 spacers used by Gansauge et al. (*Nat. Protoc.*, 8, 737-48 (2013)). An oligonuclotide containing oligoT (ten thymine in a row) is much easier and cheaper to produce than an oligonucleotide containing ten C3 spacers, and the inventors discovered that oligoT works as well as C3 spacers for the purposes of single-stranded library preparation.

Modified: CL78
(SEQ ID NO: 3)
5' AGA TCG GAA GTT TTT TTT TT 3'

A positive control (1 µL of 500 µM, synthetic ssDNA) and a negative control were included with each batch of samples.

The efficiency of ligation of cfDNA fragments to biotinylated probes and ligation of double stranded adapters to primer-extended products was estimated using quantitative PCR (Gansauge M T. et al., *Nat. Protoc.*, 8, 737-48 (2013)). On average $0.8 \times 10^9$ unique ssDNA molecules (0.02-8.2× $10^9$) were ligated and PCR amplified (8 to 15 cycles). Adjusting the extension sequence primer with a 4-N overhang on the 5' end (as in Karlsson et al. (*Genomics*, 105, 150-8 (2015)), limited the occurrence of adapter dimers to, on average, one in 1,700 sequences. Libraries were sequenced on the Illumina MiSeq or HiSeq platform (2×75 bp, average human genome coverage of 0.23×±0.06×).

The single-stranded library method of the present disclosure requires less DNA compared to conventional next-generation sequencing methods because it is more sensitive to the spectrum of type of DNA that can be collected and prepared. Conventional library preparations use double stranded adapters and are not sensitive to single-stranded, short, or damaged DNA.

The inventors found that cfDNA shorter than 100 bp becomes more accessible for sequencing following ssDNA library preparation. While conventional library preparation resulted in detection of only a few molecules of mitochondrial and microbial cfDNA with length shorter than 100 bp, the use of a ssDNA library preparation revealed an abundance of such molecules with lengths between 40 and 100 bp. The lower limit of efficient capture, as shown by the local maxima of the short fragment cfDNA, for the ssDNA library preparation, was 40-60 bp, for all subclasses (mitochondrial, microbial, nuclear genomic cfDNA), pointing to a limit set by the DNA isolation method, rather than the library preparation.

Libraries were characterized using the AATI fragment analyzer and quantified by digital PCR. Samples were pooled and sequenced on the Illumina NextSeq platform (paired end 2×75 bp) available at the Cornell Genomics Facility. Approximately 50 million paired-end reads were generated per sample. To account for sources of environmental contamination, a known template negative control (IDT-DNA synthetic oligo mix, lengths 25, 40, 55, 70 bp) was included in every sample batch and was sequenced to approximately 25% of the depth of the cfDNA extracts (~5 million fragments). Samples were prepared in batches of ~8 samples. Primary data analysis was performed with Linux command line tools. Statistical analyses were performed in R, version 3.1.2.

Analysis—Composition of the Urinary Microbiome.

Raw sequencing data in a fastq format were transferred to a lab-owned server. Low quality bases and Illumina-specific sequences were trimmed (Trimmomatic-0.32, (A. M. Bolger et al., *Bioinformatics*, vol. 30, 2114-2120, 2014)). Reads from short fragments were merged and a consensus sequence of the overlapping bases is determined using FLASH-1.2.7. Reads were aligned (Bowtie2, very sensitive mode (B. Langmead et al., Nat Methods, vol. 9, no. 4, 357-359, 2012)) against the human reference (UCSC hg19). Unaligned reads were extracted, and human coverage is calculated using the non-redundant reads (SAMtools 0.1.19 rmdup (H. Li et al., *Bioinformatics*, vol. 25, 2078-2079, 2009)) for normalization purposes. To derive the urine microbiome, reads were BLASTed (NCBI BLAST 2.2.28+) to a curated list of bacterial and viral reference genomes (W. J. Kent, *Genome Res*, vol. 12, 2002). Short reads were assigned to specific taxa using a maximum likelihood algorithm that takes into account the ambiguity of read mapping (L. C. Xia, et al., *PLoS One*, vol. 6, no. 12, e27992, 2011), as in (I. De Vlaminck, et al., *Proc. Natl. Acad. Sci.*, vol. 112, no. 43, 13336-13341, 2015), (I. De Vlaminck et al., *Cell*, vol. 155, 1178, 2013). The relative abundance of higher level taxa were determined on the basis of the genomic abundance at the strain or species level.

In confirming the presence of high relative abundance microbial communities, GINI index filtering was used to assure that microbial reads were not aligned deeply to a single or few regions of the genome (GINI set). Metaphlan was also used to confirm the presence of the high relative abundance, pathogen-associated microbial species.

Bacterial Growth Dynamics.

The reference strain with the highest coverage was selected as representative for each bacterial species. The uniformity of sequence coverage across the selected reference with respect to the replication of origin was determined. The ratio between DNA copy number near the origin of replication and that near the replication terminus was computed and used as a measure of the genome replication rate, as in (T. Korem et al., *Science* (80-.)., vol. 349, no. 6252, 1101 LP-1106, 2015).

Nucleosome Footprints in Gene Bodies.

Paired-end reads were aligned using Burrow-Wheeler Aligner (BWA-MEM) to the hg19 human reference genome. Sequence read coverage around a list of transcription start sites (TSS) to the hg19 build, as described in (P. Ulz et al., *Nat Genet*, 2016), was determined based on BAM files using the SAMtools depth function. Nucleosomal protection at the TSS of specific genes was determined based on the loss of nucleosomal protection in a 4 kbp window centered around the TSS.

Proportion of Donor Specific DNA in Urine.

The fraction of donor specific cfDNA in urine and plasma samples was estimated using approaches that have been modified from (A. J. Wolfe et al., *J. Clin. Microbiol.*, vol. 50, no. 4, 1376-1383, 2012) and (T. M. Santiago-Rodriguez et al., *Front. Microbiol.*, vol. 6, 14, 2015) to allow for donor estimates in the absence of donor genotype information. Many samples in the study had sex-mismatched, donor-recipient pairs. Following adapter trimming and quality filtering, reads were aligned to the human genome build hg19. Human-aligned reads were processed using HMM-copy, binning the genome into windows of 500 bp to adjust for mappability and GC content. Using the HMMcopy R package, the donor fraction was determined as follows:

Male donor: $D=2Y/A$

Female donor: $D=1-(2Y/A)$

D refers to donor fraction, Y refers to the Y chromosome coverage and A refers to the autosomal coverage (the mean coverage of all 22 chromosomes).

SNP-genotyping information obtained from a recipient pre-transplant whole blood sample can be used to distinguish donor- and recipient sequences for non-gender matched transplants.

SNP genotyping of whole blood/tissue genomic DNA allows comparison of cell-free DNA to both the pre-transplant donor and host, regardless of sex and provides a more accurate measurement. In the absence of this resource, a donor fraction can be determined from sex-mismatched patients by comparing the sequencing coverage of chromosome Y. If the recipient was male and there was no female donor DNA, then the ratio of chromosome Y coverage to that of any autosome (non-sex chromosome) is 0.5. Anything less than 0.5 represents an abundance of donor (female) DNA.

The DNA methylation technique mentioned gives total tissue contributing to urine/blood, and so the amount of kidney DNA in urine may be used as a proxy for donor DNA.

Mitochondrial Donor Fraction

The mitochondrial donor fraction was determined. Briefly, genomic DNA was extracted from pretransplant donor and recipient blood in parallel and amplified the mitochondrial DNA. With the mitochondrial DNA in high abundance, the DNA was sheared to 300 bp and prepared and indexed the libraries using the NEBNext Ultra kit for Illumina. The consensus mitochondrial genomes were sequenced on one lane of MiSEQ (2×150). Following sequencing, mitochondrial-aligned cell-free DNA was compared at single base-pair resolution to SNPs identified between the donor and recipient genomes and the donor fraction was computed.

Specifically, mitochondrial consensus sequences were established for every transplant donor and recipient. DNA was extracted from whole blood samples (Qiagen DNeasy Blood & Tissue kit) collected pre-transplant. Mitochondrial DNA was selectively amplified (Qiagen REPLI-g Mitochondrial DNA Kit), and sheared to 300 bp (Covaris). Libraries were prepared for sequencing using the NEBNext Ultra library preparation, characterized (Advanced Analytical Fragment Analyzer and dPCR) and sequenced (2×250 bp, Illumina MiSeq). One million sequences led to a per-base coverage greater than 100-fold (genome size 16.5 kb), sufficient to determine subject-specific mitochondrial variants. Fastq files were trimmed (Trimmomatic (Bolger A. et al., *Bioinformatics* 30, 2114-2120 (2014)), LEADING:25

TRAILING:25 SLIDINGWINDOW:4:30 MINLEN:15) and aligned against the human reference genome [GenBank: GCA_000001305.2] using BWA-mem (Li H. et al., *Bioinformatics*, 25, 1754-60 (2009)). Sequences that mapped to the mitochondrial reference sequence (edited from [GenBank:NC_012920]) were extracted. A BCF file of SNPs was created and a FASTA consensus sequence was determined. A list of informative SNPs was created.

Microbial Control

To control for possible environmental DNA contamination, a microbial control was extracted via QiaAmp Nucleic Acid extraction, prepared, and sequenced in parallel to sample sets. The control consisted of a double-stranded oligo ladder (for sequences from 25-70 bp) at 0.25 uM eluted in water.

Antibiotic Resistance Determination 224 antibiotic resistance tests were performed on 22 matched samples belonging to patients with clinically diagnosed UTIs at New York Hospital Laboratories. All tests with the exception of three (two using Kirby-Bauer method and one using E-test, which are removed), used minimal inhibitory concentration to assess the resistance of the cultured pathogenic microbe to up to 21 antibiotic drugs.

Example 2: Urinary Cell-Free DNA Extraction and Library Preparation

Urinary cell-free DNA is comprised of chromosomal, mitochondrial, and microbial cfDNA released from host cells and microbes in the urinary tract and of plasma-derived cfDNA that passes trans-renally from the circulation into urine. Urine can be collected non-invasively in large volumes, and therefore represents an attractive target for diagnostic assays. Compared to plasma DNA, relatively few studies have examined the properties and diagnostic potential of urinary cfDNA. The urinary environment degrades nucleic acids more rapidly than plasma resulting in fewer DNA fragments that are far shorter (J. Zhang et al., *Clin. Chem.*, vol. 45, 1741-1746, 1999), consequently sequence analyses of urinary cfDNA have to date required relatively large volumes of urine (>10 ml) (Y.-H. Su et al., *J. Mol. Diagn.*, vol. 6, no. 2, 101-7, 2004), (N. B. Y. Tsui, et al., *PLoS One*, vol. 7, no. 10, 1-7, 2012). Here, the inventors applied a single-stranded library preparation technique that employs ssDNA adapters and bead ligation to create diverse sequencing libraries that capture short, highly degraded cell-free DNA (P. Burnham et al., bioRxiv, 2015), (M.-T. Gansauge et al., *Nat. Protoc.*, vol. 8, no. 4, 737-48, 2013). The inventors found that single-stranded library preparation enables robust sequence analyses of urinary cfDNA from just one ml of urine. The sequencing libraries comprised an average 3.89 billion unique molecules. The inventors assayed 123 urine samples collected from renal transplant recipients, including recipients diagnosed with bacterial UTI and BK Polyomavirus Nephropathy. Samples were sequenced to a depth of 0.5-1× (15-40 million fragments). To account for technical variability and sources of environmental contamination during the library preparation, a known-template control sample was included in every sample batch and sequenced.

Figures 1C, 1D:
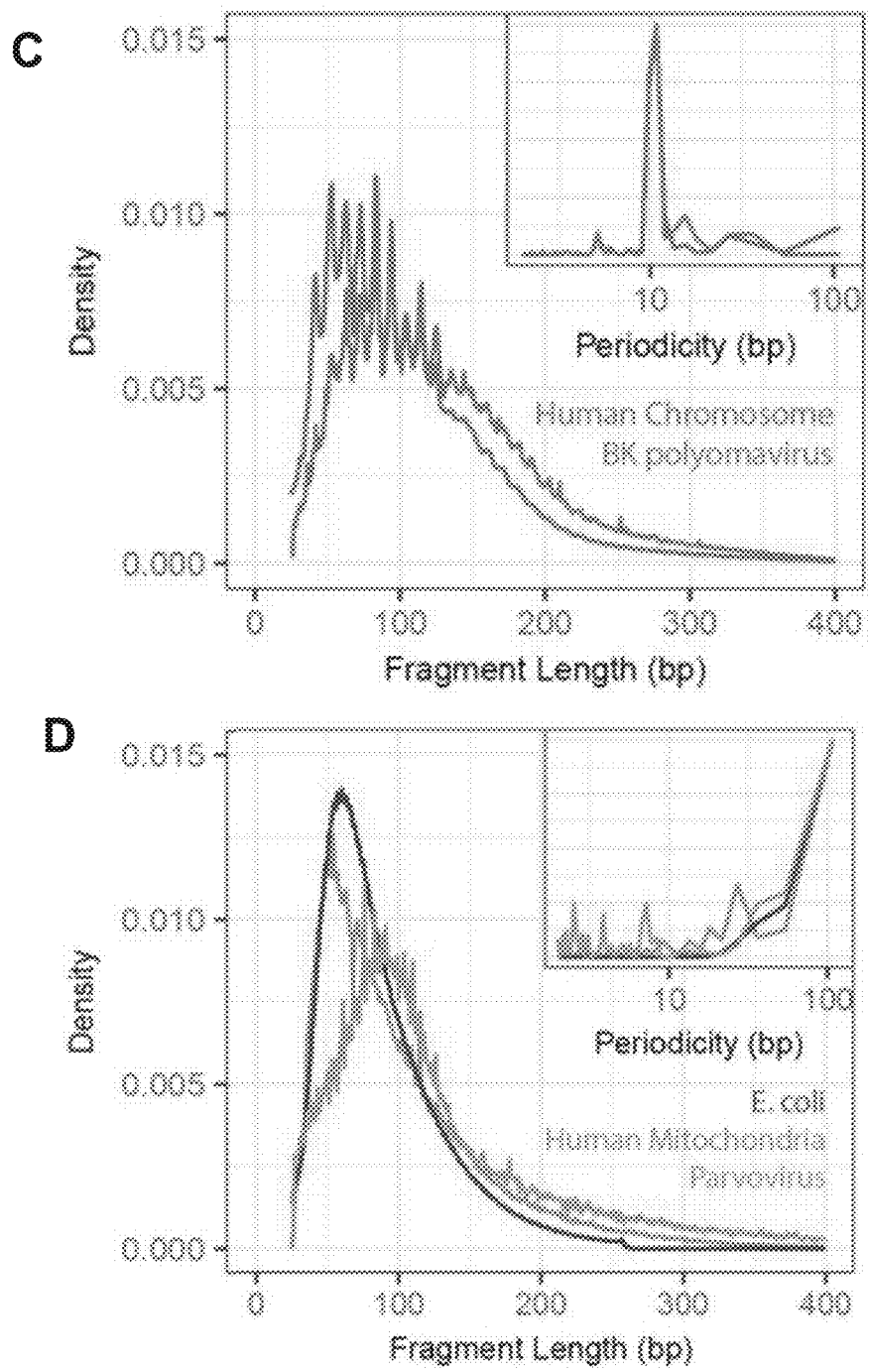

The fragment length profiles of urinary cfDNA were analyzed at single nucleotide resolution using paired-end read mapping (S. Quake, *Clin. Chem.*, vol. 58, 489-490, 2012). This analysis confirmed previous observations of the highly fragmented nature of urinary cfDNA compared to plasma cfDNA (mean fragment length for urine smaller than 100 bp) (Y.-H. Su et al., *J. Mol. Diagn.*, vol. 6, no. 2, 101-7, 2004). A 10.4 bp periodicity in the fragment length profile was observed for chromosomal cfDNA in the urine (Fourier analysis in the inlet of FIG. 1C), consistent with the periodicity of DNA-histone contacts in nucleosomes. Polyomavirus is known to hijack histones of infected host cells, and to form minichromosomes after infection. The fragment length profiles of BK Polyomavirus DNA in urine reflected this pathobiology, and indicated a predominant nucleosomal conformation of Polyomavirus cfDNA in urine (FIG. 1C). A similar nucleosomal footprint was not observed for bacterial and mitochondrial cfDNA, and cfDNA arising from Parvovirus, which was expected given the non-nucleosomal compaction of the genomes that contribute these cfDNA types (FIG. 1D). These data demonstrate that analyses of the structure of cfDNA can be used to learn about the pathobiology of pathogens and may enable to infer life cycles or infection stages.

Example 3: Infectome Screening

The presence of cfDNA was assessed from bacterial and viral pathogens reported in clinical diagnostic workups. Here, previously described bioinformatic approaches were used to quantify non-human cfDNA sequences in the datasets (I. De Vlaminck, et al., *Proc. Natl. Acad. Sci.*, vol. 112, no. 43, 13336-13341, 2015). Briefly, human sequences were identified by alignment of the sequences to the human reference and removed. Remaining sequences were BLASTed against a custom database of microbial reference genomes. The relative genomic representation of different species was estimated using GRAMMy (L. C. Xia, et al., *PLoS One*, vol. 6, no. 12, e27992, 2011). In order to directly compare the measured microbial abundance across samples and species, the representation of microbial genome copies was computed, relative to the representation of host genomes in the datasets, and expressed this quantity as relative genome equivalents (RGE).

An extremely high load of BK Polyomavirus cfDNA was detected in all samples collected from patients clinically diagnosed with BK polyomavirus nephropathy BKVN corresponding to $1.623 \times 10^5$ RGE. This high load of BK derived DNA is consistent with the pathobiology of PVAN. The inventors did not find a relationship between BKPyV cfDNA and PVAN class (Drachenberg classification). Strain level analyses revealed the presence of different BK virotypes, in many cases multiple BK virotypes were detected.

Bacterial cfDNA was quantified in samples collected from patients diagnosed with bacterial UTI. For 22 out of 24 clinically positive samples (based on conventional bacterial culture), unbiased sequencing of urinary cfDNA detected the uropathogen reported in the clinical workup. The remaining discrepancies are likely explained by misidentification in bacterial culture. Further evidence was found for the frequent occurrence of bacterial co-infections. Whereas reports of bacterial culture are skewed towards species that are responsive to culture, cfDNA sequence analyses are sensitive to the full spectrum of infecting uropathogens. In just 55% of examined samples, it was found that the uropathogen reported by culture was the most prevalent pathogen in the sample. In 22 of the 24 samples the identified uropathogen was determined to be in the top five most abundant species. Furthermore, the relative genomic abundance of the clinically identified bacterial species of infection was higher than the abundance of co-occurring bacteria in UTI samples and all microbes in non-UTI and BKVN-samples.

Example 4: Cell-Free DNA Reveals Frequent Undiagnosed Viral Infections

Figures 2A, 2B:
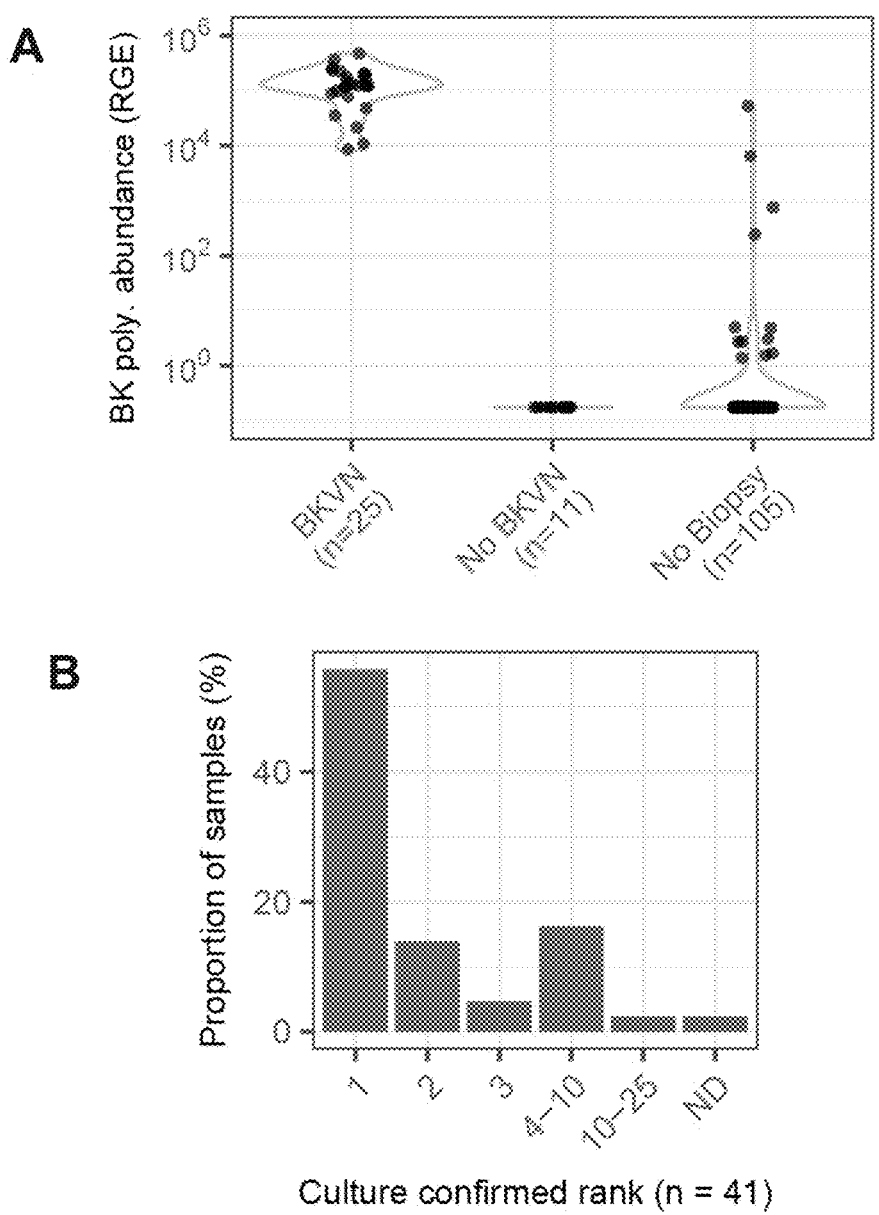
FIGS. 2A-2E. Urinary cell-free DNA confirms clinical infections and identifies co-infecting microbes. (A) Violin plots of BK Polyomavirus cfDNA sequence abundance (relative genome equivalents, RGE) for patients that are BKVN positive (determined per needle biopsy of the kidney allograft), patients that are BKVN negative (determined per biopsy), and untested patients. (B) Rank order genomic abundance for clinically reported uropathogens in the urine of patients with bacterial UTI. In approximately half of all samples, the dominant bacterial species detected in culture was the most abundant component of the cfDNA urinary microbiome. In one sample, the clinically reported agent was not detected (ND). (C) Receiver operating characteristic analysis of the performance of urinary cfDNA in identifying UTIs with common bacterial uropathogens (90 urine samples, *Klebsiella, Pseudomonas, Enterococcus*, and *Escherichia coli* UTI). (D) Most uropathogenic bacteria described as the causative agent by clinical determination had the greatest makeup of the urinary microbiome; however, nearly as many samples contained higher abundances of co-infecting microbes. (E) cfDNA reveals frequent undiagnosed viral infections in this cohort (left panel). Boxplot representation of the distribution of RGE (right panel).
Figures 2C, 2D:
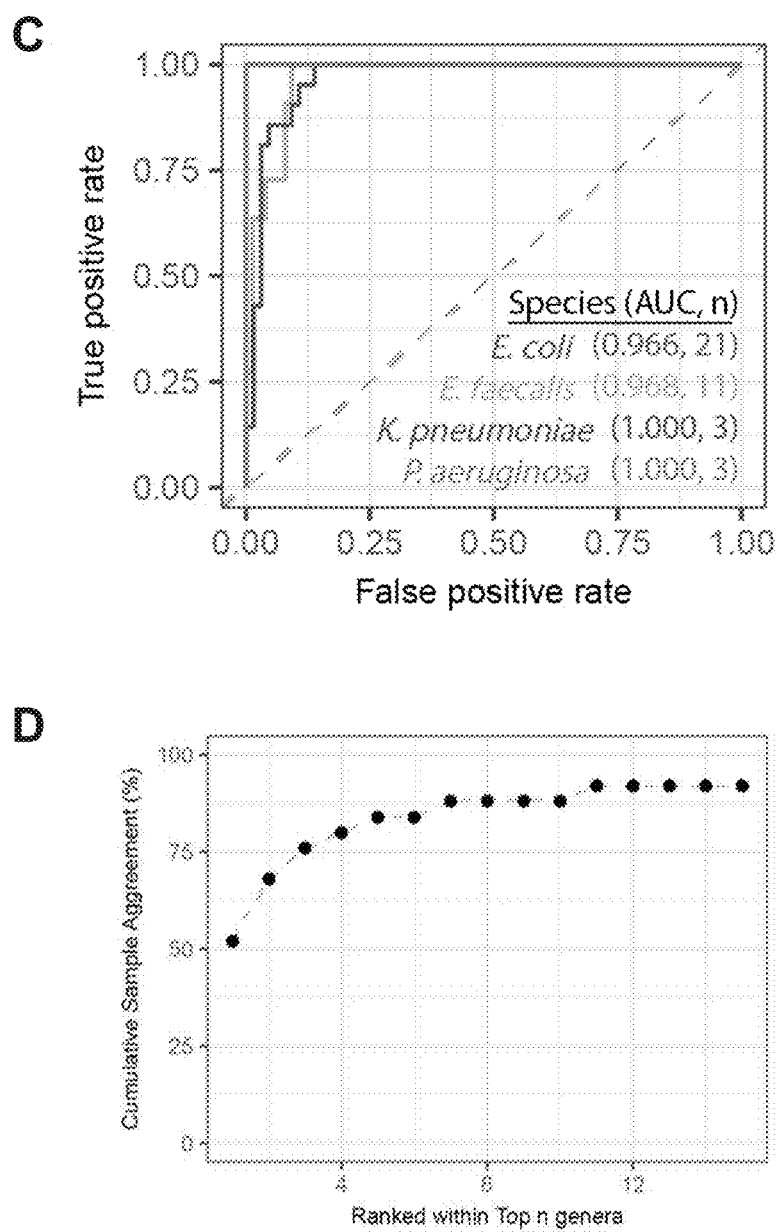
Figure 2E:
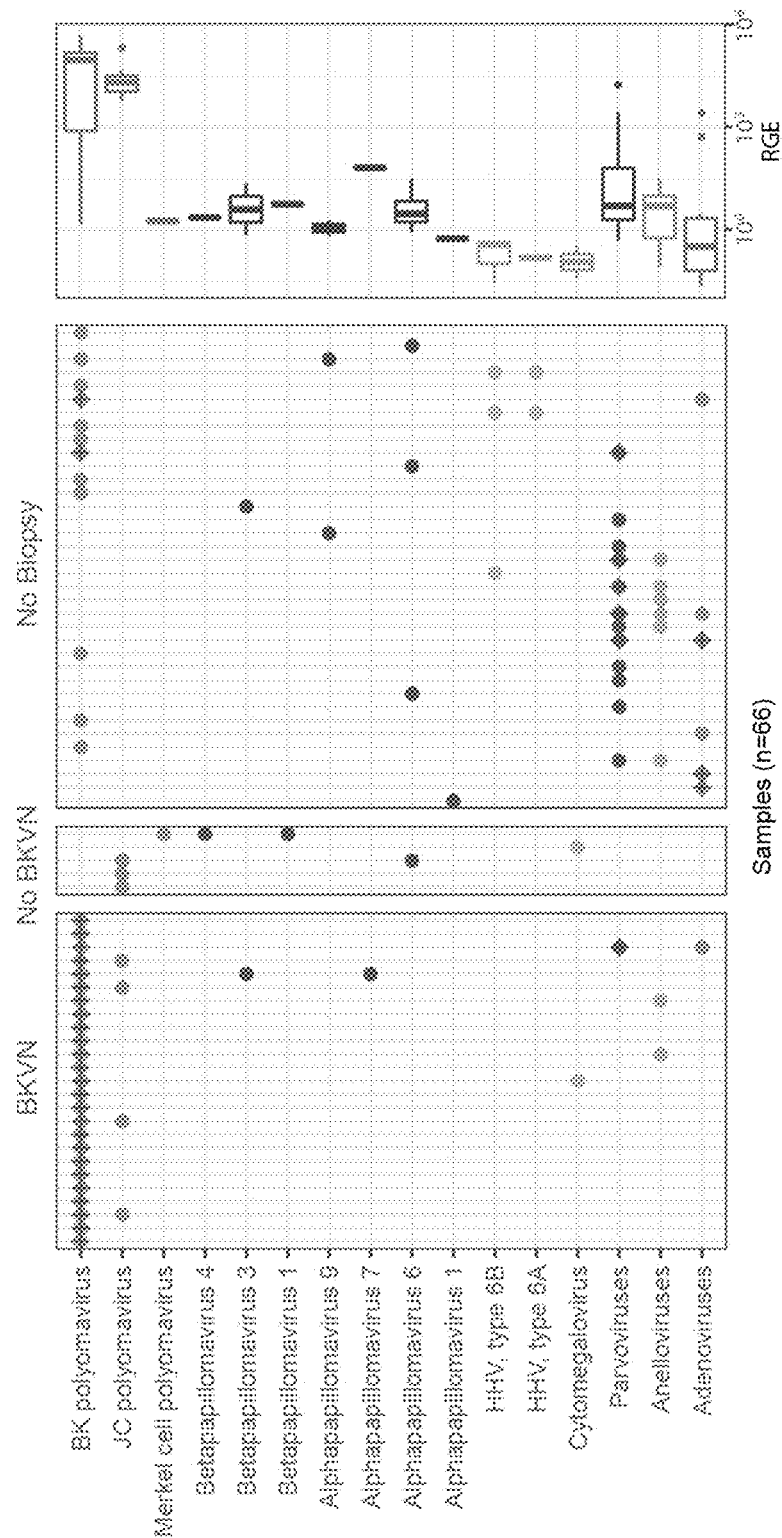

The inventors next screened for the occurrence of viral uropathogens not are not tested for in the clinical protocol currently in place in transplant hospitals. Remarkably, in more than 10% of samples collected from stable patients viral pathogens that are potentially clinically relevant were detected. Approximately two-thirds of samples (n=78) had detectable levels of clinically relevant viruses in the whole cohort of 115 urine specimens. FIG. 2E highlights the occurrence of different viruses across all samples, and reveals the frequent occurrence of infections with JC Polyomavirus, Merkel Cell Polyomavirus, several Herpesviruses and various known oncoviruses in this cohort. In addition, Parvovirus was detected in twelve samples, with a very high abundance in one sample ($1.715 \times 10^4$ RGE). Several patients were found to be simultaneously infected with different Polyomavirus species (Merkel Cell, JC Polyomavirus and BK Polyomavirus). These data illustrate the disconnect that currently exist between the frequency of clinical infection testing and the incidence of viral pathogens in this cohort of transplant patients.

Example 5: Diversity of the Urinary Microbiome

The urinary tract was long believed to be a sterile environment but recent studies have revealed that the urinary tract often harbors unique microbiota, even in the absence of urinary tract infections (A. J. Wolfe et al., *J. Clin. Microbiol.*, vol. 50, no. 4, 1376-1383, 2012; T. M. Santiago-Rodriguez et al., Front. Microbiol., vol. 6, 14, 2015; D. E. Nelson et al., *PLoS One*, vol. 5, no. 11, e14116, 2010). For 8/22 patients in the no-UTI group, we did not detect microbial DNA above background (where the background due to environmental contaminants is established based on the analysis of known-template control samples, see methods). A rich urinary tract microbiome was detected for patients with UTIs however. The diversity within the microbiome was quantified as the Shannon entropy. As expected, among different superkingdoms, population diversity decreases with known infection (whether BK polyomavirus or UTI causal agent) since the representation of that particular species is greatly enriched. However, in the cases of known UTI, it was observed that the viral diversity significantly increases compared to samples without viral nephropathy. This result is most likely due to the increased presence of phage DNA, since they have an increased population of hosts in which to replicate. These data indicate the utility of urinary cfDNA in the profiling of the urinary microbiome.

Example 6: Quantifying Bacterial Growth Rates from Cell-Free DNA

Figures 3A, 3B:
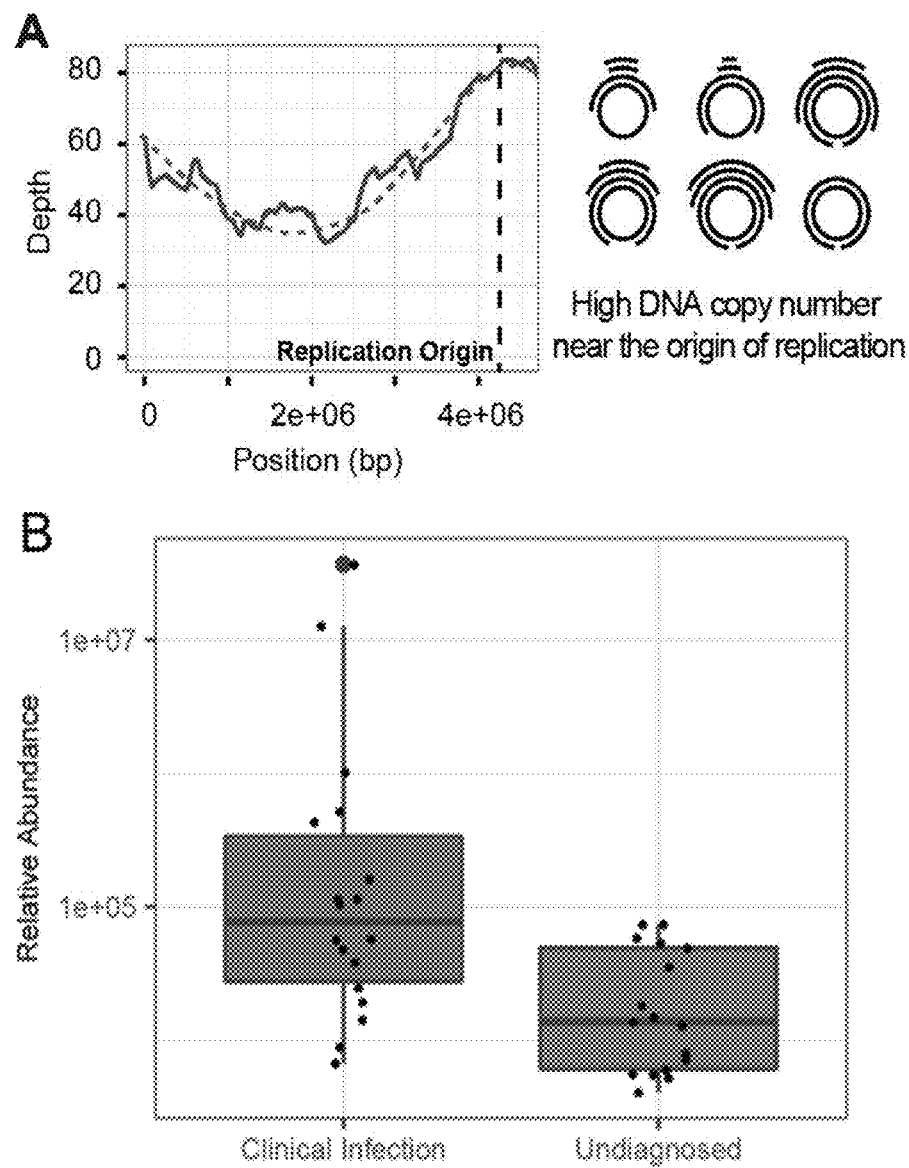
FIGS. 3A-3F. Estimating bacterial growth dynamics and detection quality. (A) cfDNA sequence coverage of the *E. coli* genome for a patient diagnosed with *E. coli* UTI. Indicative of a growing bacterial population in the urinary tract, each bacterial cell is at a different stage of genome replication. Therefore replication origin is represented the most in the library (indicated by increased depth of coverage). (B) Relative abundance of cfDNA from uropathogens reported in culture for patients with UTI (left, blue), compared to the abundance of microbial cfDNA for species detected in the urine of undiagnosed patients (orange, right). (C) Estimated genome replication rate for uropathogens reported in culture for patients with UTI (left, blue), and the replication rate of microbial species detected in the urine of undiagnosed patients (orange, right). (D) Virulence, a measure of the seriousness of an infection, defined as the product of the replication rate and the relative genomic abundance, for the groups in panels C and D. (E) Normalized bacterial genome coverage for four representative bacterial species. The coverage was binned in 1 kbp tiles and normalized. Each panel represents a single sample, with the exception of *C. acnes* for which the coverage was aggregated across 105 samples. Solid line is a loess filter smoothing curve (span=0.70). The non-uniform genome coverage for *E. coli* and *K. pneumoniae*, with an overrepresentation of sequences at the origin of replication, is a result of bi-directional replication from a single origin of replication. (F) The skew in genome coverage reflects the bacterial growth rate, where a stronger skew signals faster growth (Brown, C. T. et al, Nat Biotech, 34, 1256-1263 (2016)). Growth rates for species in twelve genera grouped by patient cohort (at least 2500 alignments). Each point indicates a bacterial species in a sample. Triangles indicate culture-confirmed bacteria by genus.
Figures 3C, 3D:
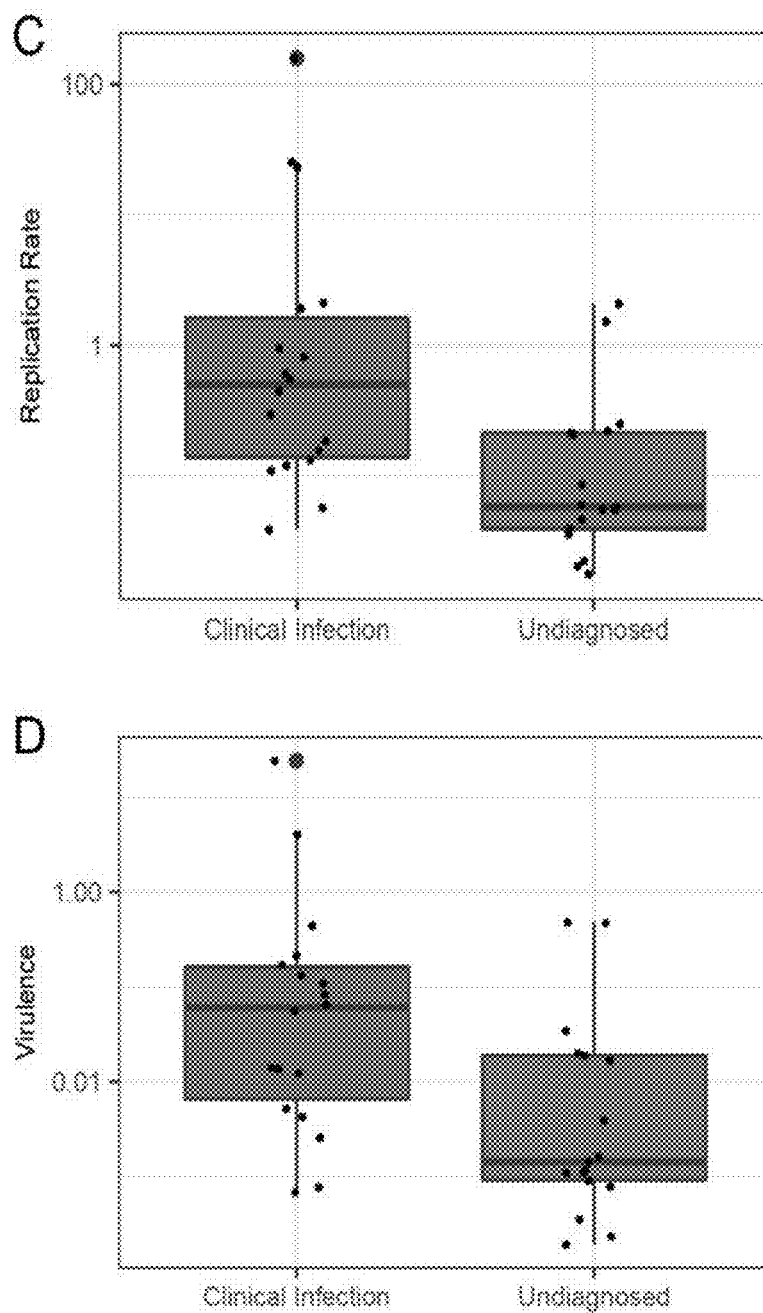
Figures 3E, 3F:
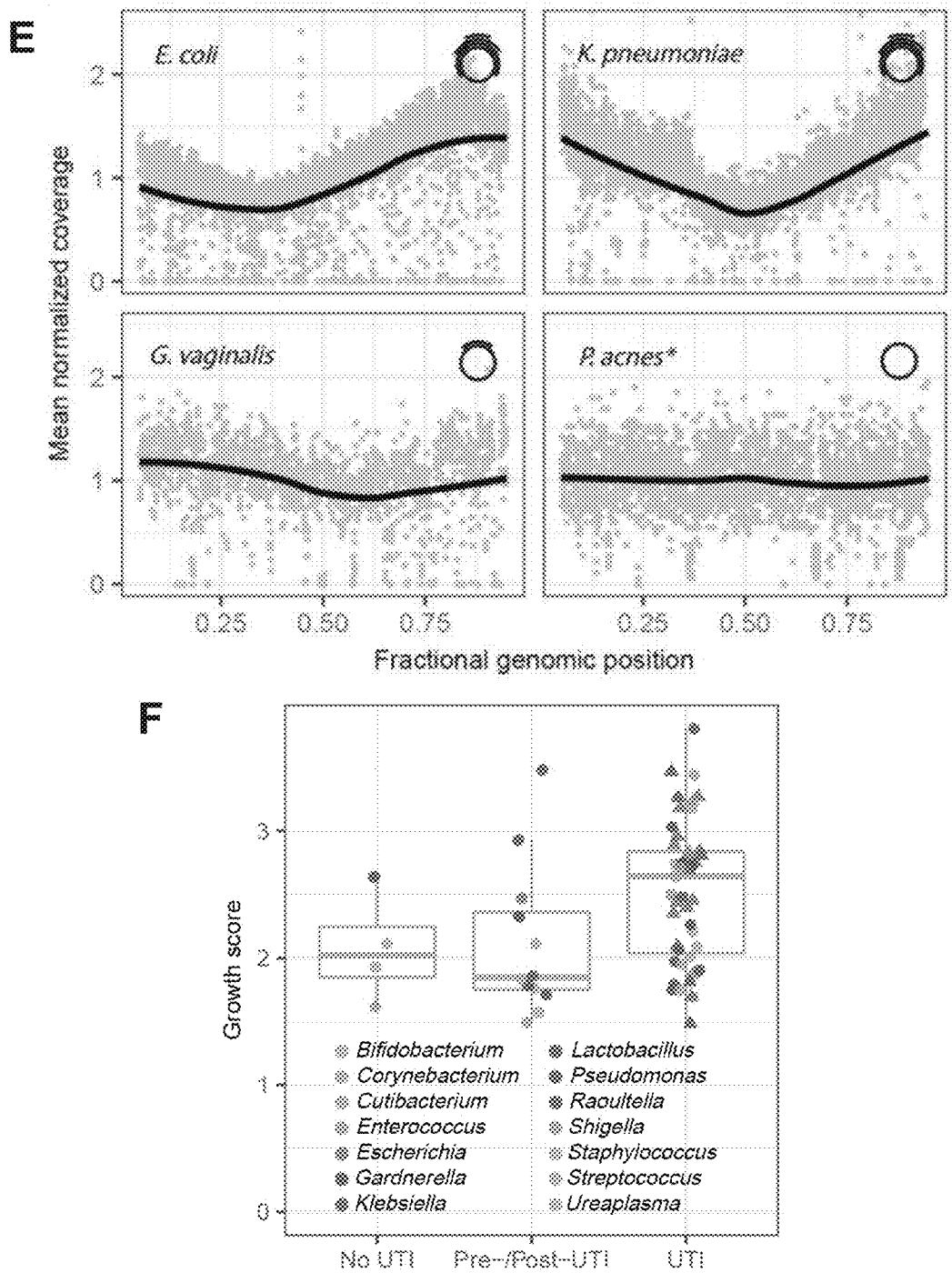

Conventional metagenomic sequencing can provide a snapshot of the microbiome, yet does not inform about microbial life cycles or growth dynamics. In a recent study, Korem et al. (T. Korem et al., *Science* (80-.)., vol. 349, no. 6252, 1101 LP-1106, 2015) reported that the pattern of sequencing read coverage across a microbial genome can be used to quantify microbial genome replication rates for microbes in complex gut microbiome communities. Here, the inventors have tested whether the concepts introduced by Korem et al, can be used to estimate bacterial growth dynamics in the scope of UTI from measurements of urinary cfDNA. FIG. 3A shows the urinary cfDNA sequence coverage of the *E. coli* genome for a kidney transplant patient diagnosed with an *E. coli* UTI. The genome coverage is highly non-uniform, with an overrepresentation of sequences close to the origin of replication, consistent with a rapidly growing bacterial population. These measurements enable estimating the presence and growth of microbes implicated in UTI. Metagenomics sequencing may be used to determine the replication rate and growth dynamics of various strains in a bacterial community without the need for an annotated genome.

The relative genomic abundance was determined for uropathogens reported in bacterial culture for patients diagnosed with UTI, and compared to the abundance of any bacterial species detected in the urine of patients that were not diagnosed with UTI (no clinical indication of infection, bacterial culture not performed). It was found that the relative abundance of the uropathogens reported in culture compared bacterial species detected in the urine of asymptomatic individuals.

Example 7: Antibacterial Resistome

Figure 4A:
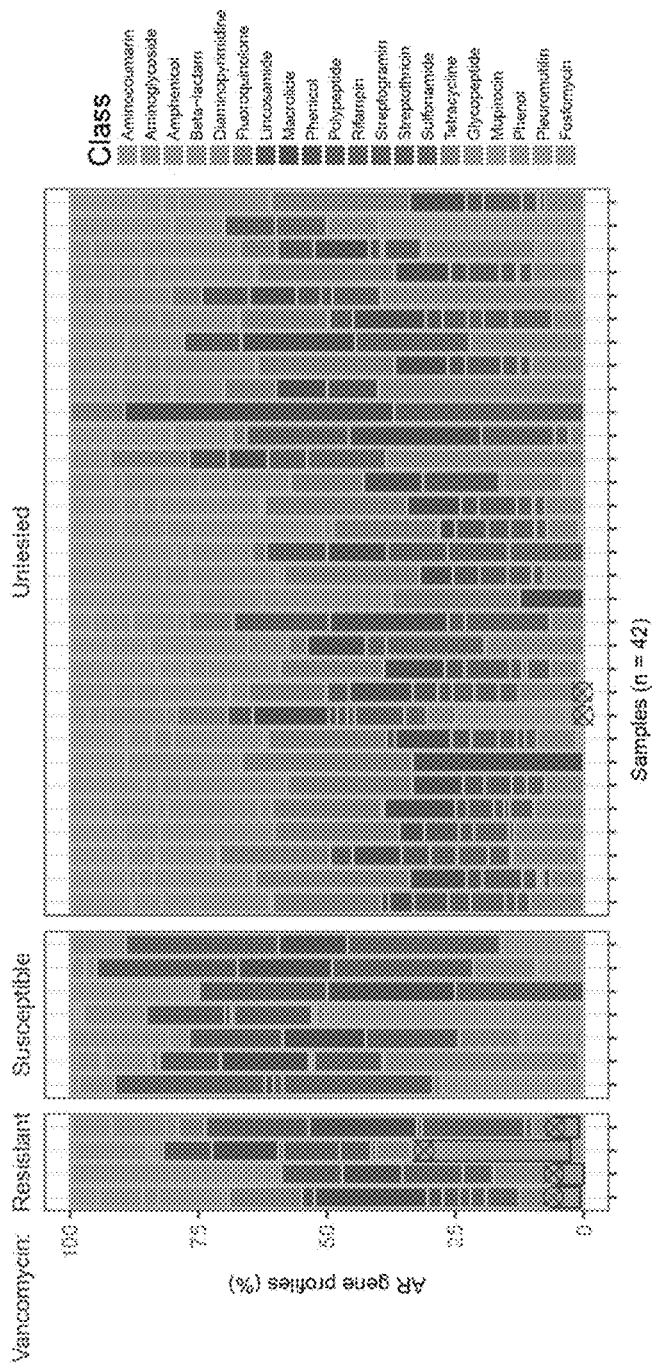
FIGS. 4A-4C. cfDNA based antimicrobial resistome profiling. (A) For 25 samples with clinically confirmed UTIs, AR gene profiling reveals the presence of genes conferring resistance to various drug classes. Genes that confer resistance to glycopeptide class antibiotics (including vancomycin) are highlighted in red outlines. (B) A breakdown of each antibiotic resistance class indicates that the presently disclosed pipeline identifies most samples with high abundance of beta-lactam and fluoroquinolone resistance genes (colored by clinically infecting microbe). (C) A clustering of the samples in (a) reveals three distinct groups and correctly identifies samples from patients who had clinically-identified, vancomycin-resistant, enterococcal UTIs.
Figures 4B, 4C:
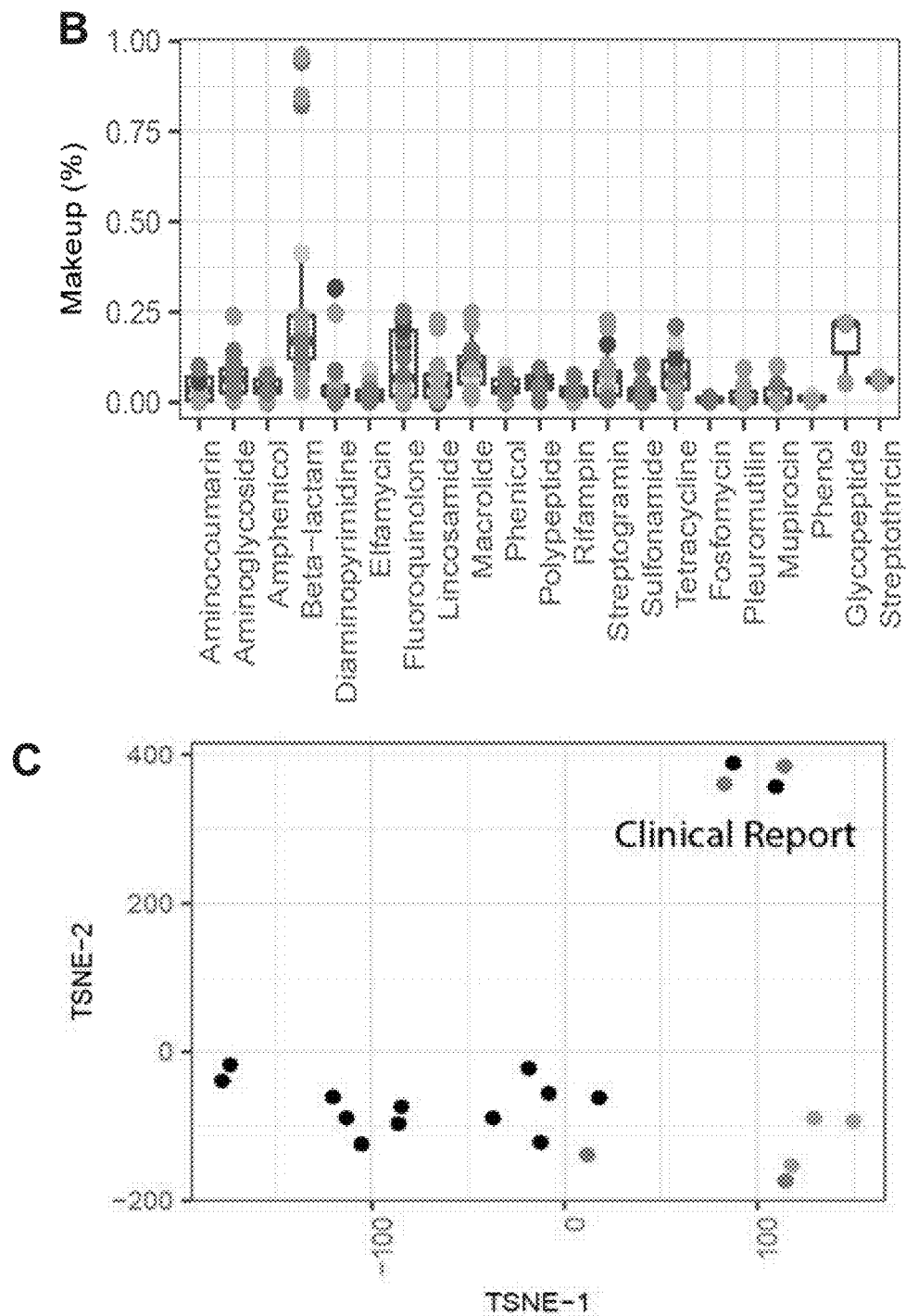

For twenty-one samples collected from patients with clinically confirmed UTIs the inventors determined the relative abundance of genes conferring resistance to several classes of antibiotics. Non-human sequences were aligned against known antibacterial resistance genes and mutations using the Comprehensive Antibiotic Resistance Database (CARD) Resistance Gene Identifier (RGI) software (A. G. McArthur et al., Antimicrob. *Agents Chemother.*, vol. 57, no. 7, 3348-3357, 2013). RGI reports aligned ABR genes, which we aggregated and called against a desperate CARD reference that indicates the drug resistance conferred by the given gene. A breakdown of each antibiotic resistance class indicates that this pipeline correctly identifies most samples with high abundance of beta-lactam and fluoroquinolone resistance genes (FIG. 4B, colored by clinically reported uropathogen). Unsupervised clustering revealed three distinct groups and correctly identified samples from patients who had clinically-identified, vancomycin-resistant, enterococcal UTIs (FIG. 4C). These data indicate significant potential to predict the efficacy of antibacterial drug therapies based on measurements of urinary cell-free DNA.

Example 8: Host Response to Infection

Figure 5A:
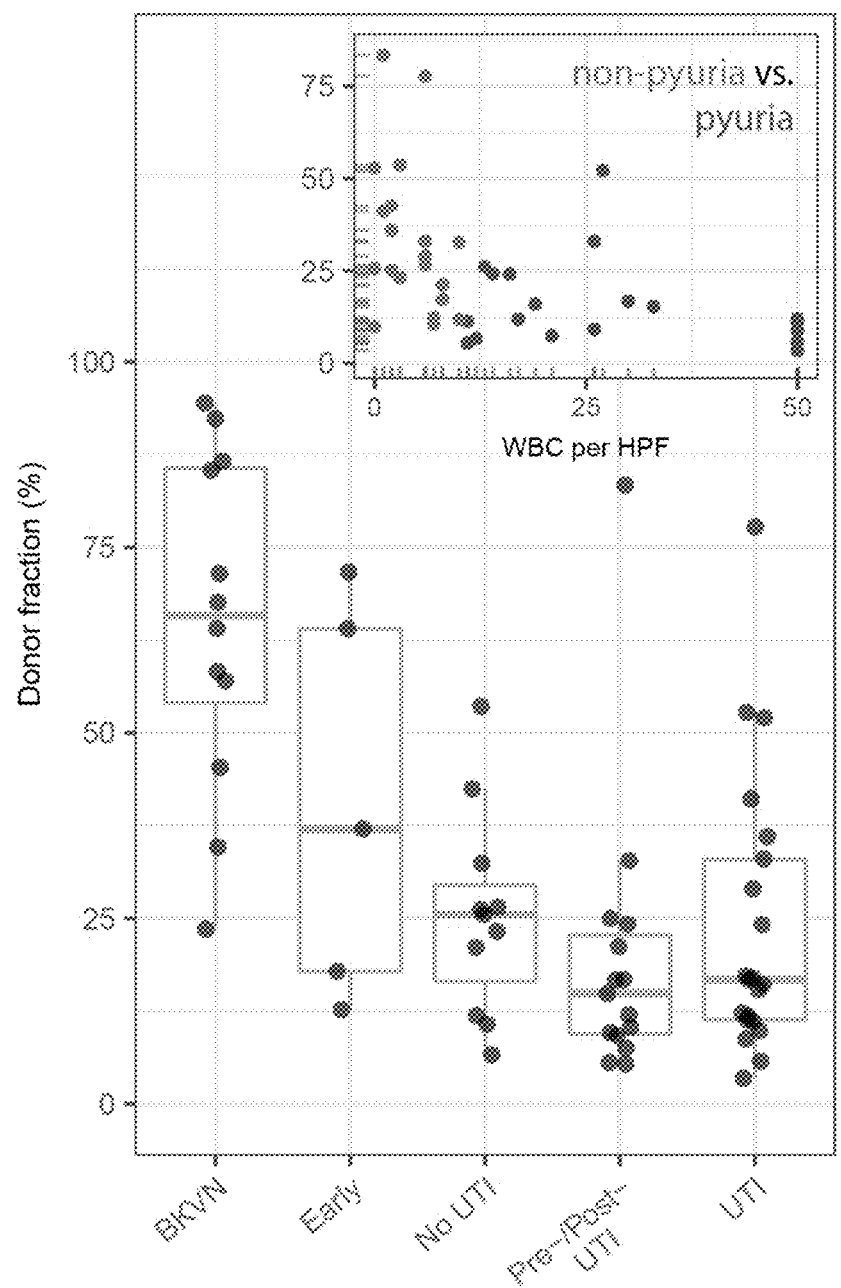
FIGS. 5A-5C. The host response to infection from urinary cell-free DNA. (A) Proportion of donor-specific cfDNA in samples from patients that are BKVN positive per kidney allograft biopsy (BKVN), in samples collected in the first five days after transplant surgery (Early), samples collected from patients that UTI negative per culture (No UTI), samples collected before and after UTI (Pre-/Post-UTI) and samples collected at the time of UTI diagnosis (UTI). Two outliers in Pre-/Post-UTI and UTI groups correspond to the same patient, who suffered an acute rejection episode in the months prior. Low donor fractions in the Pre-/Post-UTI and UTI groups are likely due to immune cell presence in the lower urinary tract; patients with higher white blood cell counts have lower donor fractions (inset, red indicates pyuria (the condition of urine containing white blood cells or pus)). (B) Absolute abundance of donor cfDNA in the urine of patients not diagnosed with infection in the first month post-transplant. (C) Genome coverage at the transcription start site (TSS), binned by gene expression level across all (n=141) samples in the study. FPKM=Fragments per Kilobase of Transcript per Million mapped reads, an RNA-seq measure of gene expression.

Next, the host response to viral and bacterial infections was examined. First, the proportion of transplant donor specific cfDNA in the urine was quantified. Recent work has identified donor derived cfDNA in plasma as a marker of graft injury in heart, lung, liver and kidney transplantation (I. De Vlaminck, et al., *Proc. Natl. Acad. Sci*; vol. 112, no. 43, 13336-13341, 2015), (I. De Vlaminck et al., *Sci. Transl. Med.*, vol. 6, no. 241, 241ra77, 2014; M. Grskovic et al., *J. Mol. Diagn.*, vol. 18, no. 6, 890-902, 2016; Y. M. D. Lo et al., *Lancet*, vol. 351, no. 9112, 1329-1330, 2016). Here, donor cfDNA was quantified in urine for sex-mismatched donor recipient pairs (FIG. 5A, methods). Elevated levels of donor cfDNA were observed for patients diagnosed with BKVN (mean donor fraction 58.3%) compared to stable patients (mean 41.4%, samples collected within 10 days after transplant excluded). The release of donor DNA reflects severe cellular and tissue injury in the graft, which is a hallmark of BKVN. There was modest correlation between the calculated donor fraction and the number of BK genome copies detected in the sample (Spearman correlation 0.523, p<0.05). In addition, it was found that the level of donor DNA in the first few days after transplant was elevated, consistent with early graft injury, and in line with the inventors' earlier observations in heart and lung transplants. The relative and absolute proportion of donor specific urinary cfDNA was tracked in the first few days after transplantation for a small subset of patients. An elevated level of donor DNA was observed in the first few days after transplant (both quantified as a relative and absolute amount of donor DNA). This initial elevated level of donor DNA quickly decayed to a lower baseline level, similar to previous observations in heart and lung transplantation (I. De Vlaminck, et al., *Proc. Natl. Acad. Sci.*, vol. 112, no. 43, 13336-13341, 2015), (J. Beck et al., *Clin. Chem.*, vol. 59, 1732-1741, 2013), (I. De Vlaminck et al., *Sci. Transl. Med.*, vol. 6, 241ra77, 2014). In contrast to patients diagnosed with Polyomavirus infection, for patients diagnosed with bacterial UTI, a decreased proportion of donor DNA was observed as compared to stable individuals. This is likely explained by an increased number of recipient immune cells in the urinary tract. Indeed, comparison to clinical urinalysis indicates that white blood cell count is negatively correlated with the donor fraction (FIG. 5A, inlet).

Figures 5B, 5C:
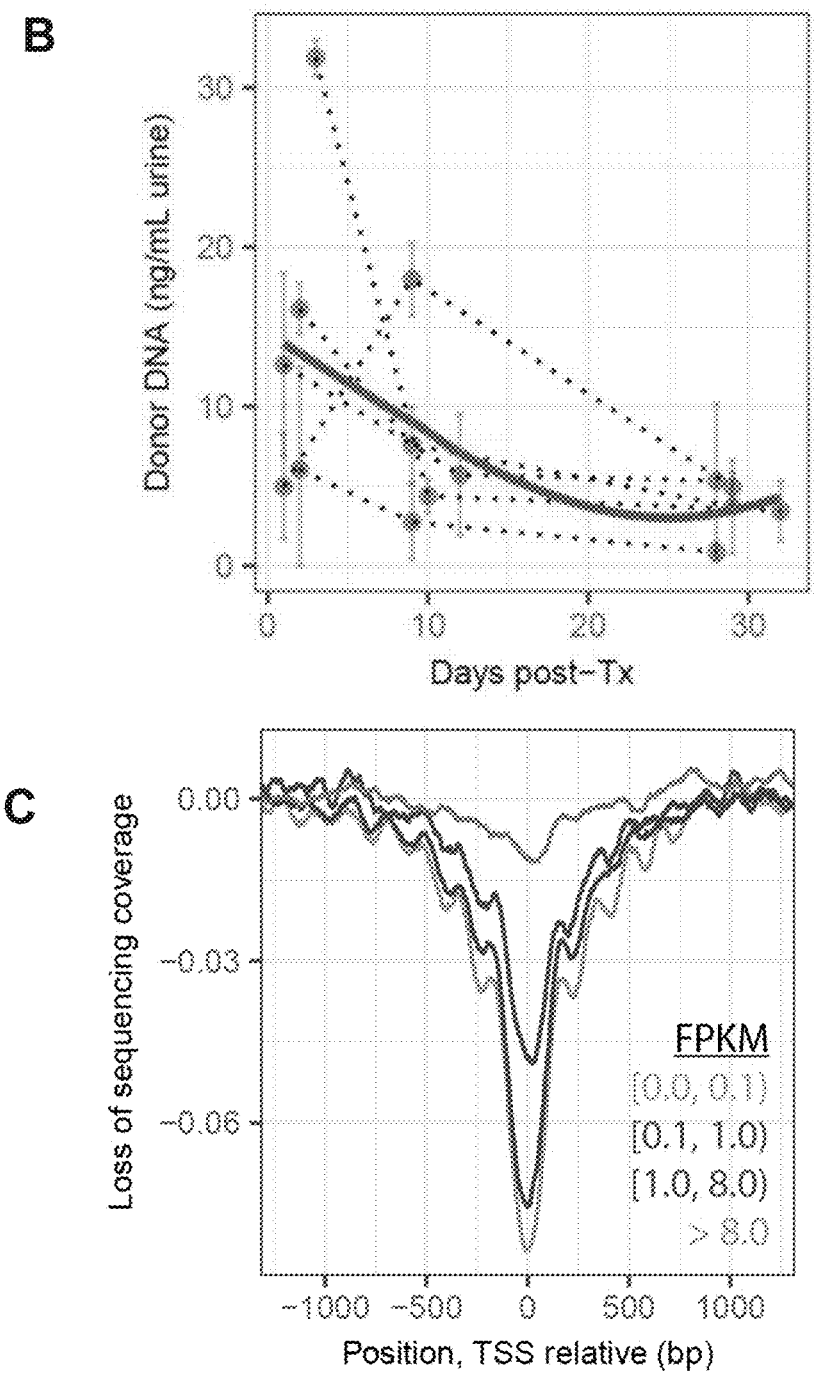

Two studies of the properties of cfDNA in plasma by Ulz et al. (P. Ulz et al., *Nat Genet*, 2016), and Snyder et al. (M. W. Snyder et al., *Cell*, vol. 164, no. 1, 57-68, 2016) have demonstrated that the structure of chromatin in gene promoters are conserved within circulating cfDNA. Ulz et al. employed whole-genome sequencing of plasma DNA to show that nucleosomal occupancy at transcription start sites (TSSs) results in different read depth coverage patterns for expressed and silent genes. Here, the inventors found that the footprints of nucleosomes in gene promoters and transcriptional regulatory elements are conserved within urinary cfDNA (FIG. 5C), and that the extent of nucleosomal protection is proportional to gene expression. Measurements of nucleosomal depletion can serve as a proxy for gene expression, and may be used to investigate host-pathogen interactions in the scope of urinary tract infection in more detail.

For a small subset of these patients (n=8), the inventors performed donor and recipient mitochondrial whole genome sequencing and compared the mitochondrial-aligned cfDNA to the respective donor and recipient consensus mitogenomes, as previously described. The inventors determined the donor fraction by comparing cell-free DNA fragments to SNPs between the donor and recipient. The inventors found that the graft is the predominant source of mitochondrial urinary cfDNA. Mitochondrial DNA is recognized by pattern recognition molecules that alternatively sense bacteria, not surprising, perhaps, in view of the hypothesized endosymbiotic origin of mitochondria. Recent data confirm a role for extracellular mitochondrial DNA as a powerful Damage Associated Molecular Pattern (DAMP): Elevated levels of mtDNA in plasma have been reported in trauma, sepsis and cancer and recent studies have shown that mitochondrial DNA released into the circulation by necrotic cells can contribute to neutrophil-mediated organ injury. The potential role of DAMPs in pathogenesis of allograft rejection however remains understudied. It is clear that surgical trauma, ischemic injury, infection and rejection lead to cellular injury in the graft and it is conceivable that the release of DAMPs that accompanies this injury promotes many of the harmful immunologic responses observed in solid organ transfer (SOT). Molecular techniques to track DAMPs in urine released in the scope of kidney graft injury may provide a non-invasive window into the potential role of these molecules in the pathogenesis of immune-related complications.

The present disclosure provides a strategy to identify and assess infections of the urinary tract based on profiling of urinary cfDNA and omics analysis principles. The disclosure shows that different layers of clinical information are accessible from a single assay that are either inaccessible using current diagnostic protocols, or that require parallel implementation of a multitude of different tests. In nearly all samples with clinically reported viral or bacterial infections of the urinary tract, cfDNA identified the causative agent of infection. cfDNA furthermore revealed the frequent occurrence of both viral and bacterial co-infections that remain unidentified in current clinical practice. In more than 10% of analyzed samples, including samples from patients regarded clinically stable, undiagnosed viral infections that are likely clinically relevant were detected. The assays and methods presented here therefore have the potential to become valuable research tools that will enable monitoring of the frequency of occurrence of viral infections in kidney transplant cohorts, and their potential impact on long term outcomes in kidney transplantation. Deeper sequencing can further find use in the identification of mutations conferring more successful infections or previously unidentified uropathogens.

Cell-free DNA in the blood circulation is to large extent cleared from the blood via the kidneys. Analyses of urinary cell-free DNA can therefore reveal infections that occur throughout the body, and are not limited to the detection of infections of the urinary tract. Blood collection requires a minimally invasive procedure, whereas urine can be collected entirely noninvasively. In this light, urine may prove an ideal specimen type for whole-body infection analysis based on unbiased sequencing of cell-free DNA.

Beyond measurements of the abundance of different components of the microbiome, urinary cfDNA provides information about uropathogen phenotypes. The present disclosure demonstrates that analyses of the structure of microbial genomes allow estimating bacterial replication rates, thereby providing dynamic information from a single snapshot. Metagenomic analysis of urinary cfDNA can furthermore be used to predict the efficacy of antibacterial drug therapies. The sequencing data was compared to a curated database of genes conferring antibacterial resistance (ABR), and agreement was found between the alignments to ABR genes and clinical resistance reports determined via minimum inhibitory concentration measurements on urine cultures. Linking determinants of bacterial resistance to specific strains is challenging for complex infections. UTI in kidney transplantation offers a good test ground for such analyses, given the absence of a normal microbiome in the urinary tract, the potential to perform serial analyses and the access to relevant clinical information on drug resistance.

More than 15,000 patients receive life saving kidney transplants in the US each year. Viral and bacterial infections of the urinary tract occur frequently in this patient group and often lead to serious complications, including graft loss and death. In the general population, UTI is the most frequent medical problem that patients present with in medical offices. Unbiased sequencing of cell-free DNA offers a comprehensive window into the infectious disease biology of UTI and can be a valuable future diagnostic tool to monitor and diagnose UTIs in kidney transplantation and in the general population. The methods disclosed herein can be robustly implemented on low volumes of urine (1 ml or less) and will benefit of technical advances in DNA sequencing that continue to reduce cost and assay turnaround time.

Example 9: Peritoneal Dialysis Fluid Analysis

The inventors have discovered that next generation sequencing of cell-free DNA from plasma and urine can be used to diagnose bacteremia (the presence of bacteria in the blood) and bacteriuria (the presence of bacteria in urine). The inventors collected and sequenced cell-free DNA from the peritoneal dialysis fluid of several patients with and without infection to determine the viability of cell-free DNA as a diagnostic to predict and monitor peritonitis.

Briefly, cfDNA was extracted from peritoneal dialysis (PD) fluid in a manner similar to plasma and subsequently prepared for sequencing using custom library preparation (Burnham et al., *Scientific Reports*, vol. 6, Article No: 27859, 2016). The libraries were multiplexed and sequenced using Illumina Nextseq, and raw reads were aligned to both the human genome and a database of microbial genomes.

Figures 6A, 6B:
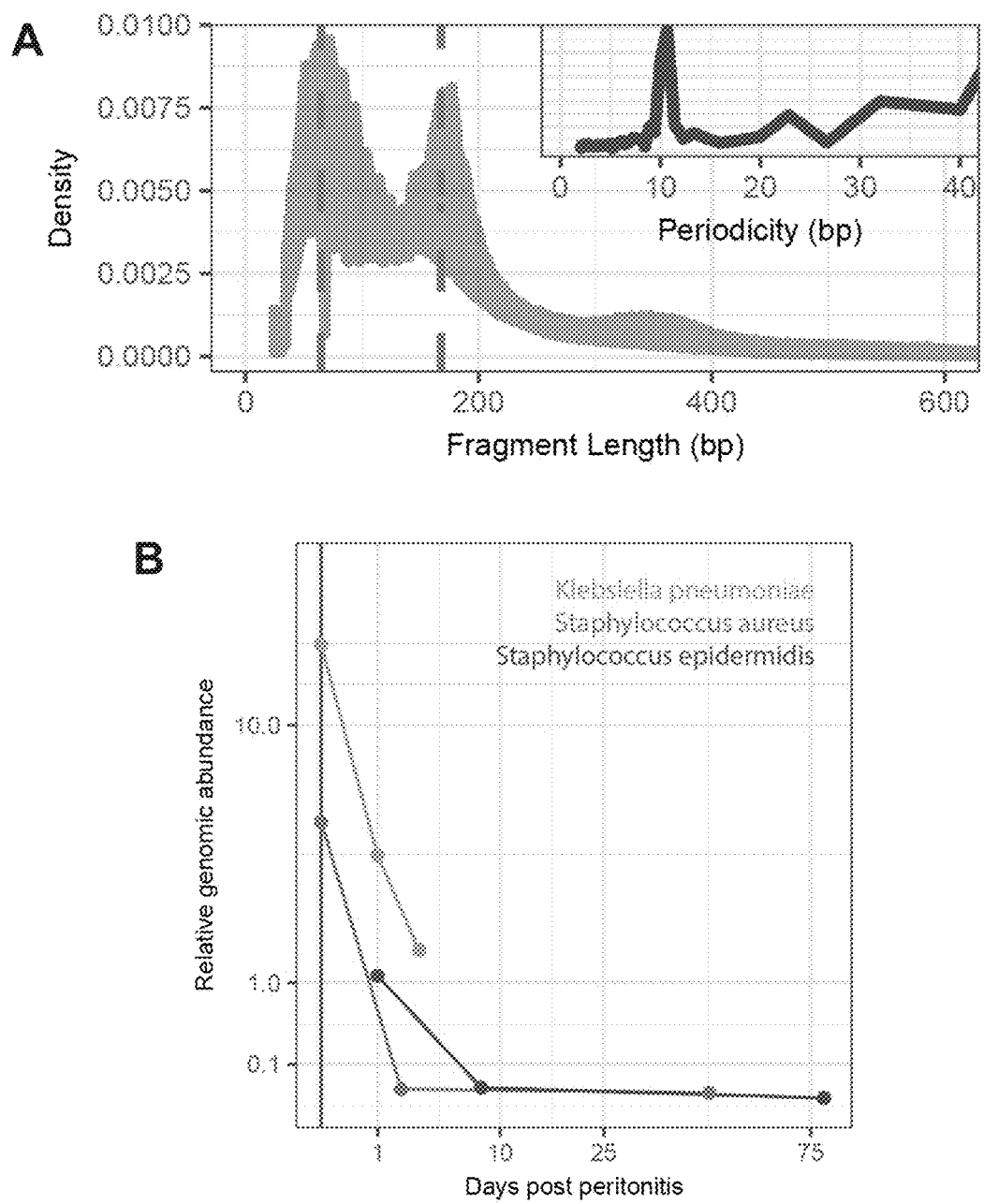
FIGS. 6A-6C. (A) Distributions of fragment length from cell-free DNA is depicted for 8 samples (grey), with the mean distribution of those samples shown in yellow. A Fourier transform between the two dashed lines is depicted (inset, blue), showing a periodicity of 10.4 bp—indicative of nucleosome associated DNA. (B) Amount of pathogenic cfDNA for three patients following peritonitis diagnosis for three different species of bacteria. (C) For each three patients and corresponding infections in FIG. 6B, alignment across each bacterial genome is depicted. Wave-like structures showing heightened coverage at the origin of replication, here at 0.0 fractional genomic position, and shallow coverage at the terminus (0.5 fractional genomic position), indicate a high fraction of the population was under replication at time of sample collection—as in *K. pneumoniae, t*=0 days and *S. aureus, t*=0 days.

Analysis of fragment lengths showed a high variability in cfDNA degradation beyond the nucleosome-bound length (167 bp). Roughly 10%-50% of cfDNA was shorter than 100 bp in any given sample in the pilot study (FIG. 6A). As in urinary cfDNA, the inventors observed repeating local maxima with a periodicity 10.4 bp for PD fluid cfDNA shorter than 167 bp in a histogram of fragment lengths (FIG. 6A, inlet). Such structure is indicative of cfDNA sequentially unbinding from nucleosomes as it is degraded. In cases of infection, identification of bacterial cfDNA in PD fluid showed correlation with clinical reports of three cases of culture-confirmed peritonitis from both gram-positive and gram-negative bacterial pathogens (FIG. 6B). In the cases analyzed, high levels of cell-free DNA corresponding to bacterial infection subsided in the first few days following antibiotic administration (FIG. 6B).

Figure 6C:
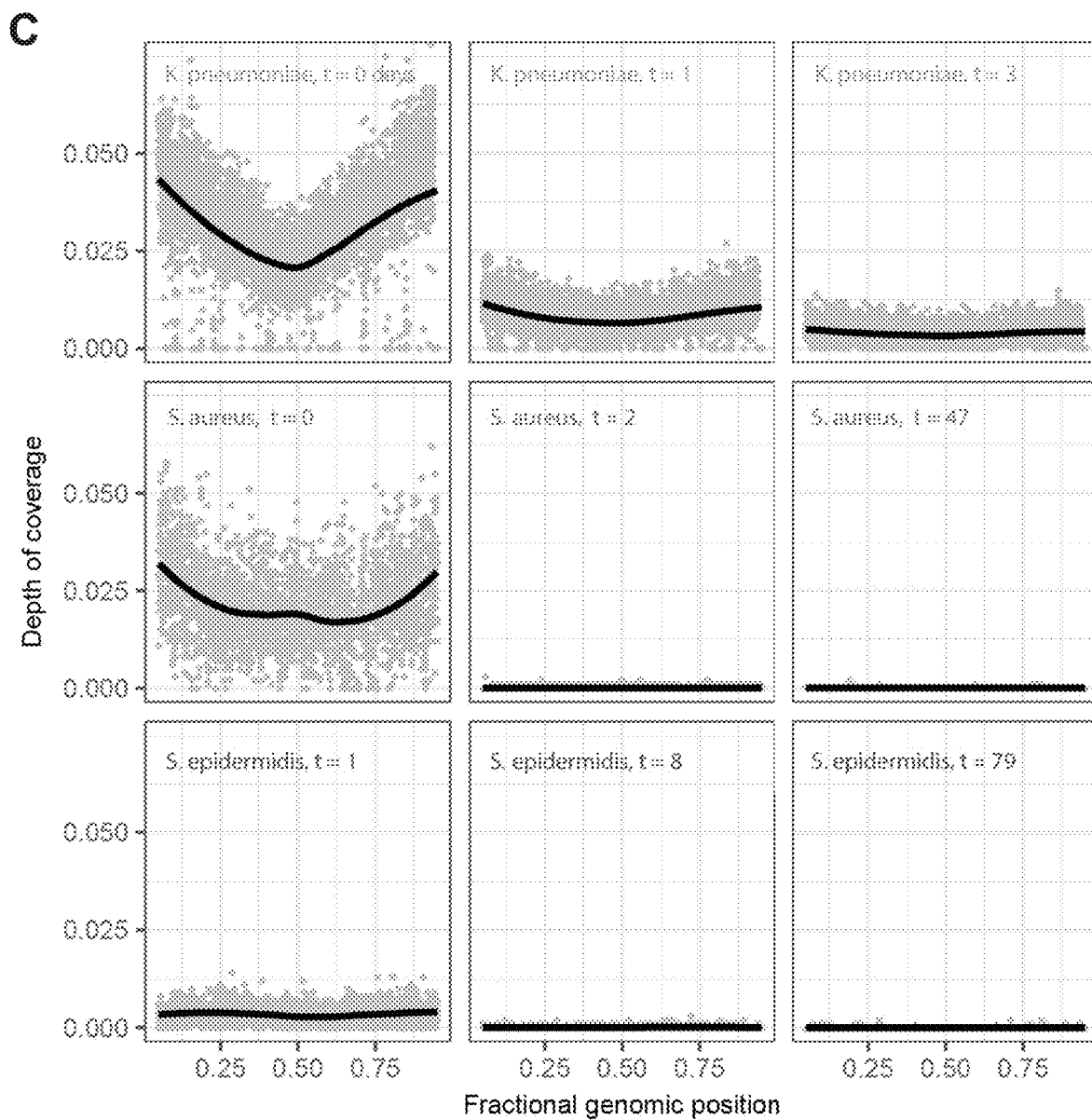

The inventors were also able to sequence the bacterial genomes at a high enough depth to observe replication dynamics of the population. In FIG. 6C, structures with higher coverage at the origin (0.0 fractional genomic position) relative to the terminus (0.5 fractional genomic position) revealed a dynamic, growing population in which most bacteria are replicating their genome at time of death. Weeks after treatment, coverage of the bacterial genomes was low and coverage is more uniform; which indicated that a population that is not longer replicating. Such structures have been well noted in the extraction of genomic DNA from bacterial communities (Korem et al., *Science*, 349 (6252):1101-1106. 2015), and the inventors noted the phenomenon for urinary cfDNA attributed to uropathogens.

Example 10: DNA Methylation Analysis

DNA methylation in mammals is a naturally occurring phenomenon where a methyl group is covalently bound to a cytosine nucleotide. DNA methylation is involved in gene silencing (Curradi et al., *Mol. Cell Bio.*, vol. 22 (9), pages 3157-3173, 2002) and its patterns throughout the genome are tissue specific (Lehmann-Werman et al., *PNAS*, vol. 113 (13), E1826-E1834, 2016). The inventors showed that cell-free DNA (cfDNA) can be used to quantify organ damage and identify pathogens in patients who have underwent solid-organ transplantation. However, regular sequencing methods cannot distinguish infection from infectious disease or quantify a systemic host response. The inventors have used methylation patterns in urinary cell-free DNA from kidney transplant patients to identify the presence of pathogens as well as quantify contributing tissue proportions as a measurement of the host response.

Once libraries have been sequenced, the subsequent reads are mapped back to a modified human reference genome that has accounted for the conversion of cytosines. As such, if a sequenced read indicates a cytosine (C), and its mapped position is also a C, it can be deduced that the original DNA was methylated. If a thymine (T) is read in the sequence and the reference contains a C, it can be deduced that the original DNA was an unmethylated cytosine. Deeper sequencing will allow for multiple reads to be mapped back to the same genomic location, therefore approaching a more statistically-significant methylation score.

cfDNA from urine samples were extracted according to manufacturer's recommendations (Qiagen, cat #55114), bisulfite treated (Zymo, cat # D5031) and were subsequently prepared for sequencing according to previously developed methods (Burnham et al., *Scientific Reports*, vol. 6, Article No: 27859, 2016). The bisulfite treatment allows for the conversion of unmethylated cytosines into uracils. During PCR amplification of the DNA, those uracils are amplified as thymines. Following sequencing, reads are aligned to both the human genome as well as the BK polyoma genome (DUN strain). Comparing sequenced reads to the human reference genome allows to infer whether a cytosine was methylated or not. See FIG. 7A.

Figure 7B:
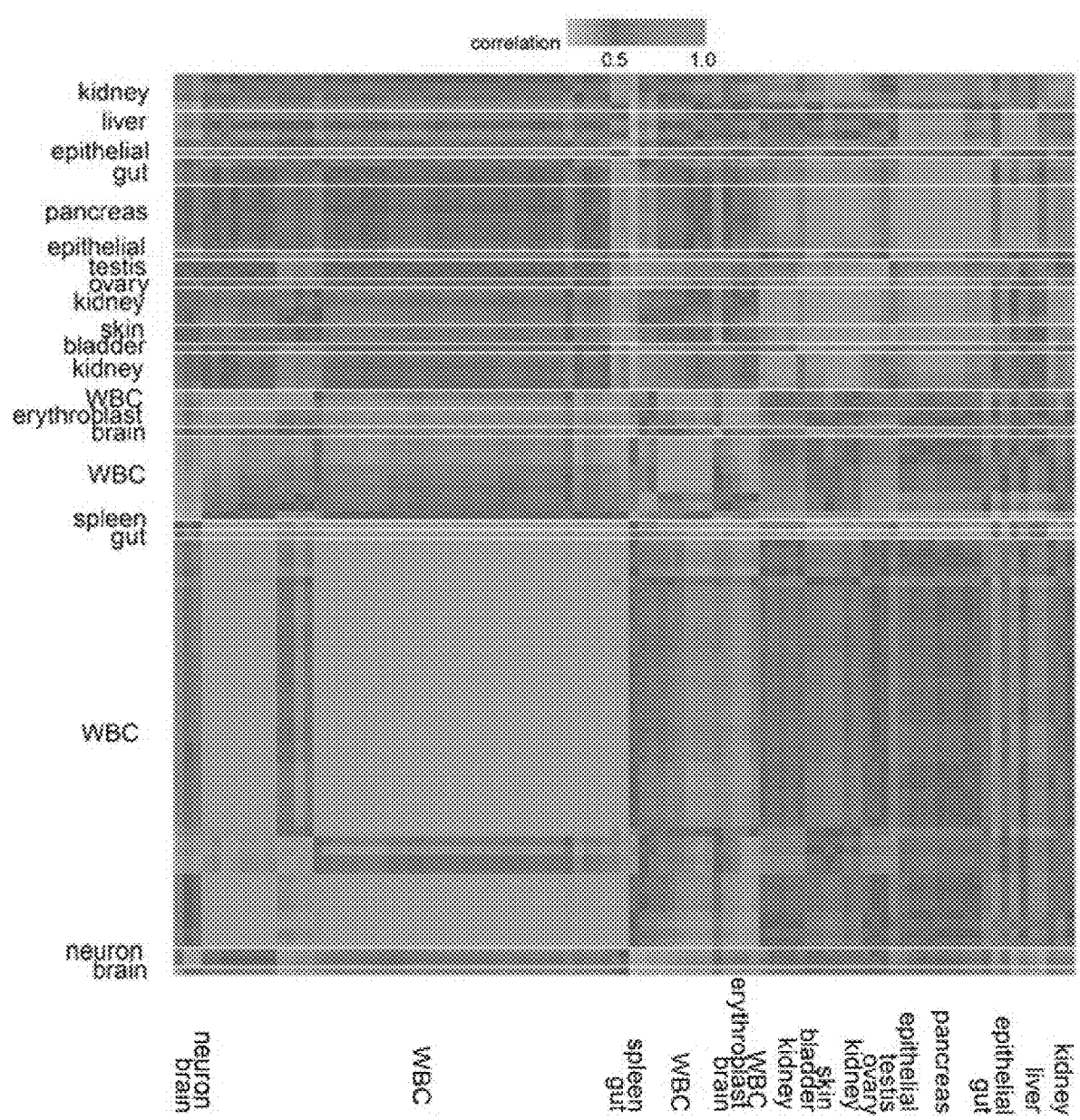
Figures 7C, 7D, 7E, 7F:
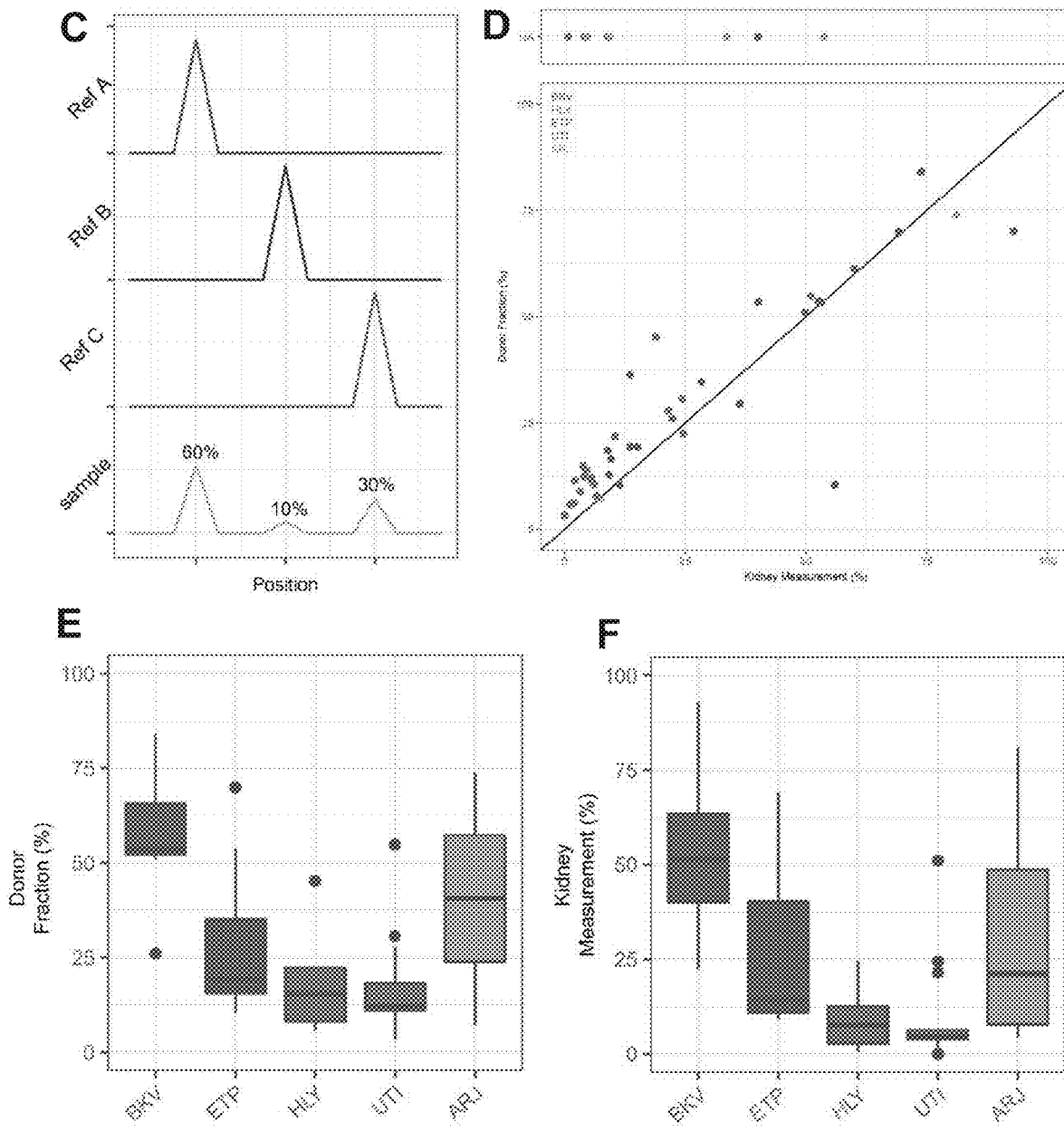

The inventors then created a reference panel of publicly available tissues that underwent whole-genome bisulfite sequencing and measured the correlation between each tissue (FIG. 7B). Tissue proportions were measured in the samples by comparing the human-aligned reads to the reference panel using quadratic programming (FIG. 7C).

Specifically, the following generalized equation was used:

$$\begin{bmatrix} M_{11} & M_{21} & \ldots & M_{N1} & 1 \\ M_{12} & M_{22} & \ldots & M_{N2} & 1 \\ \vdots & \vdots & \vdots & \vdots & \vdots \\ M_{1(L-1)} & M_{2(L-1)} & \ldots & M_{N(L-1)} & 1 \\ M_{1L} & M_{2L} & \ldots & M_{NL} & 1 \end{bmatrix} \begin{bmatrix} p_1 \\ p_2 \\ \vdots \\ p_N \\ \varepsilon \end{bmatrix} = \begin{bmatrix} O_1 \\ O_2 \\ \vdots \\ O_N \\ O_{N+1} \end{bmatrix}$$

where M is the methylation score for N tissues over L 500 bp windows. $\varepsilon$ refers to possible noise, p refers to each tissue's contribution to the cfDNA found in urine (which must always be greater or equal to zero). O refers to the observed methylation after sequencing. The inventors also set a parameter that the sum of all tissue contributions cannot exceed 100%.

As there are more genomic windows (~100,000,000) than there are reference tissues for any given sample, the inventors can select the windows which minimize the error defined by the absolute difference between the calculated methylation proportions and the observed methylation. This set of equations can be solved using quadratic programming. For this study, the equations were solved using R programming and the LimSolve package (Soetaert, Karline, Karel Van den Meersche, and Dick Van Oevelen. "*Package limSolve, solving linear inverse models in R.*" See http://cran.r-project.org/web/packages/limSolve (2009)).

The tissue methylation reference panel was created by using tissues that were whole-genome bisulfite sequenced by various laboratories and where the methylation scores were made publicly available. 97 tissues were selected for this study and include white cell types (eosonophils, neutrophils, etc.), kidney, liver, pancreas, amongst others.

The measurements were validated by comparing kidney-derived DNA with the donor fraction in sex-mismatched patients (FIGS. 7D-7F). Donor fractions can be calculated by counting the proportions of X and Y chromosomes when the kidney donor's sex is different than the recipients and has been described herein.

Figure 7G:
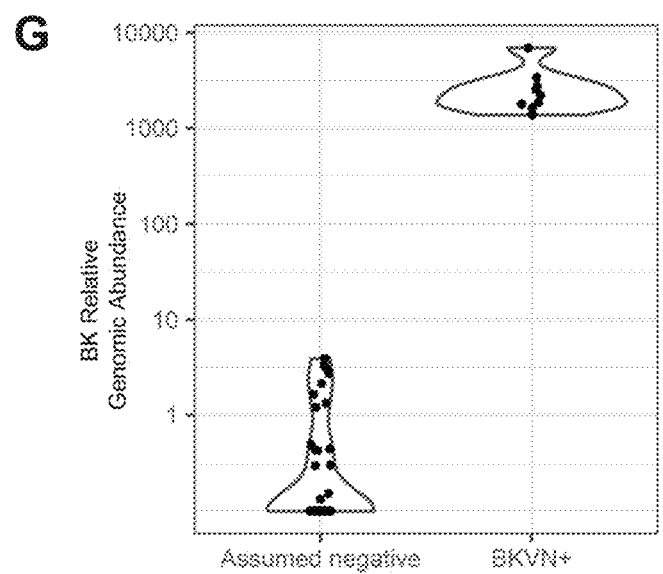
Figure 7H:
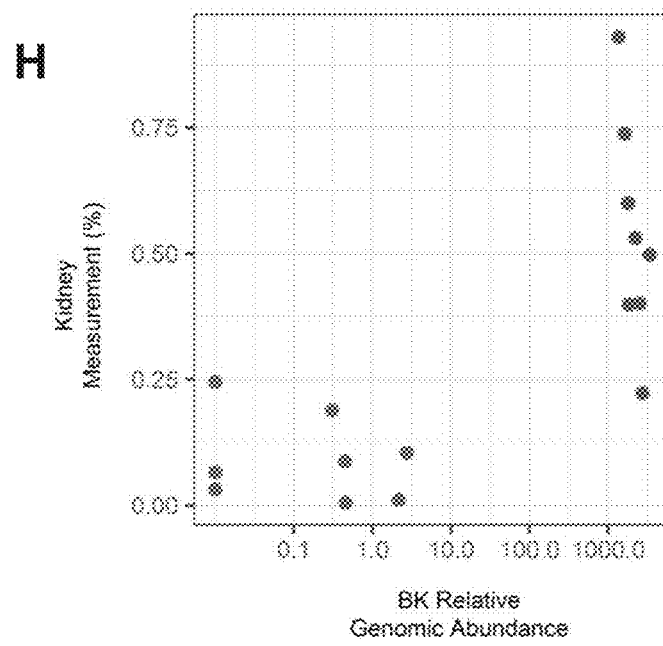
Figure 7I:
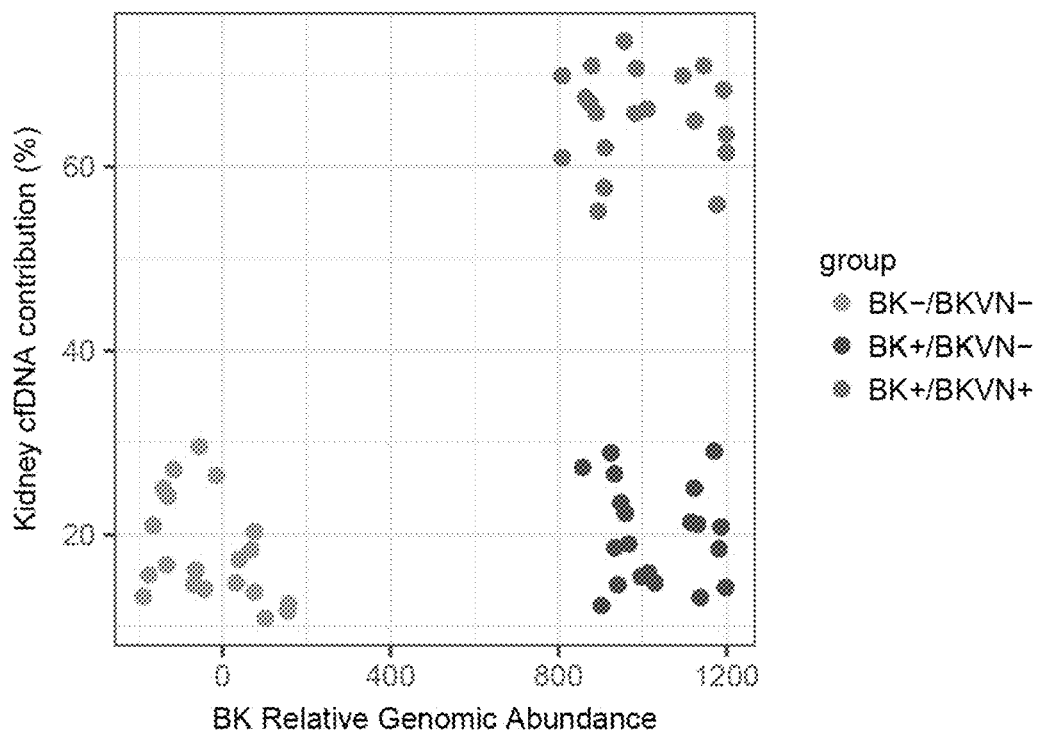
Figure 7J:
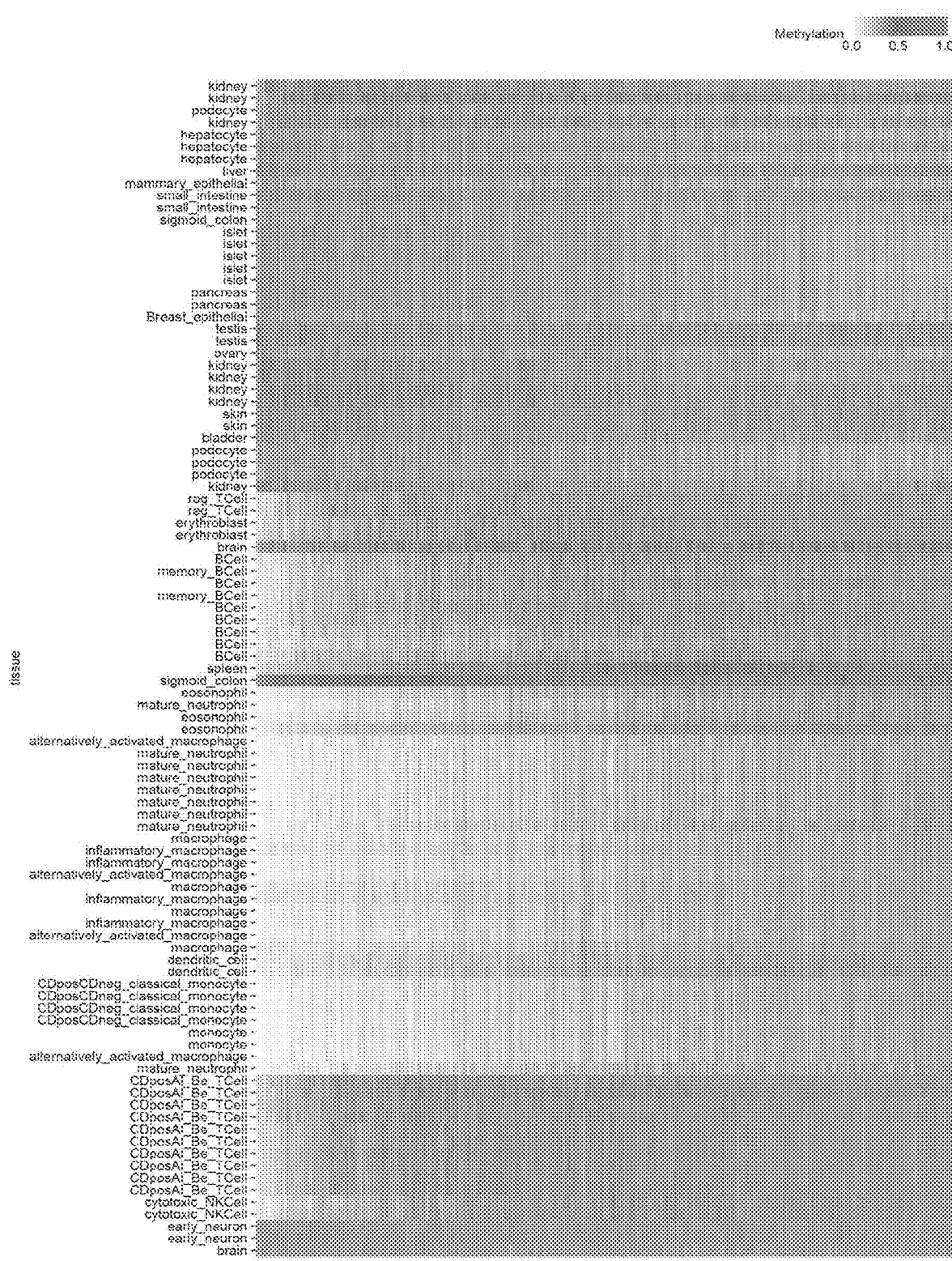

The relevant genomic abundance of BK polyomavirus was compared to kidney-derived DNA in order to demonstrate that the method can be used as both a metagenomic and host measurement assay (FIGS. 7G-7H).

As shown above, it is possible to use standard sequencing to detect bacterial and viral DNA. However, as this type of DNA is not often cytosine-methylated, bisulfite treatment results in a decrease in base-pair complexity (from a 4 base pair system to a 3 base pair system). The inventors discovered that this decrease in base-pair complexity does not hinder the ability to detect pathogens.

Briefly, the inventors aligned sequenced reads from WGBS samples that did not map to the human genome (assumed to be non-human) and aligned them to the BK genome (BK virus-DUN strain). The inventors then looked at the relative genomic abundance of the BK virus compared to the human using the following calculation: Relative genomic abundance=depth of sequencing of the BK genome/depth of sequencing of the human genome, where depth of sequencing relates to the amount of reads aligning to the genome of interest.

These results demonstrated that pathogen detection can be accomplished using WGBS instead of standard sequencing, making WGBS a powerful tool for pathogen detection as well as measuring tissue of origin.

What is claimed is:

1. A method comprising:
   (a) subjecting cell-free DNA (cfDNA) isolated from a sample from a human host subject to bisulfite treatment, wherein the sample is selected from the group consisting of a urine sample and a peritoneal dialysis fluid sample;
   (b) preparing a single-stranded sequencing library of the bisulfite treated cfDNA;
   (c) obtaining the sequences of the cfDNA in the sequencing library;
   (d) identifying host DNA sequences by aligning the sequences from step (c) to a human reference genome, and identifying and removing sequences that align to the human reference genome, wherein the remaining sequences are the nonhuman DNA sequences;
   (e) identifying microbial DNA sequences by aligning the non-human DNA sequences to a database of microbial reference genomes to identify microbial DNA sequences;
   (f) obtaining the methylation profile of the cfDNA based on the sequences obtained in step (c) and
   (g) determining the tissue of origin of the host DNA based on the methylation profile of the host DNA.

2. The method of claim 1, wherein the subject is selected from the group consisting of a kidney transplant recipient and a peritoneal dialysis patient.

3. The method of claim 1, wherein the DNA molecules in the sequencing library vary between 25 to 350 bp in length.

4. The method of claim 1, further determining that the subject is undergoing an infection if an increased number of microbial sequences is detected from the sample, compared to a sample of a healthy control.

5. The method of claim 4, wherein the infection is a bacterial infection.

6. The method of claim 5, further comprising determining that bacteria causing the bacterial infection are actively replicating if the coverage of the bacterial genome is high and a higher coverage is observed at the bacterial replication origin relative to the rest of the bacterial genome; and determining that bacteria causing the bacterial infection are not replicating if the coverage of the bacterial genome is low and uniform.

7. The method of claim 5, further comprising identifying an antibiotic resistance status of the bacteria by aligning the sequences to a database of antibiotic resistance genes.

8. The method of claim 7, further comprising administering the subject with an antibiotic, wherein the antibiotic is not identified as one of the antibiotics the bacteria are resistant to.

9. The method of claim 4, wherein the infection is a viral infection.

10. The method of claim 1 wherein the determining the tissue of origin comprises aligning the methylation profile of the sequences of the host DNA to a methylation reference panel.

11. The method of claim 1, wherein the subject is a kidney transplant recipient and the method further includes detecting donor DNA in the cfDNA sample.

12. The method of claim 11, wherein the detection of donor DNA is achieved by the steps comprising:
   (i) aligning the DNA sequences from step (c) to a human reference genome; and
   (ii) identifying donor DNA from single nucleotide polymorphisms (SNPs) in the sequences that align to the human reference genome that differ from the SNPs in the host genome, wherein is host genome SNP information is derived from a pre-transplant whole blood sample of the subject.

13. The method of claim 12, further comprising determining the fraction of donor DNA based on the SNP information.

14. The method of claim 11, wherein the donor and the recipient are of different sexes and the detection of donor DNA is achieved by the steps comprising:
   (i) aligning the DNA sequences from step (c) to a human reference genome; and
   (ii) determining fraction of the donor DNA by the ratio of the coverage of the Y chromosome and the coverage of an autosome.

15. The method of claim 14, wherein the donor is a female and the recipient is a male, it is determined that there is donor DNA in the sample if the ratio of chromosome Y coverage to that of the autosome is less than 0.5; it is determined that all the cfDNA in the sample is donor DNA if the ratio of chromosome Y coverage to that of any autosome is zero; and it is determined that there is no donor DNA in the sample if the ratio of chromosome Y coverage to that of any autosome is exactly 0.5.

16. The method of claim 14, wherein the donor is a male and the recipient is a female, and it is determined that there is donor DNA in the sample any DNA sequences align to chromosome Y; it is determined that all the cfDNA in the sample is donor DNA if the ratio of chromosome Y coverage to that of any autosome is exactly 0.5; and it is determined that there is no donor DNA in the sample if the ratio of chromosome Y coverage to that of any autosome is exactly zero.

17. The method of claim 4, wherein the method further comprises quantifying the proportion of host DNA from a tissue as a measurement of damage to said tissue resulting from the infection.

* * * * *